United States Patent
Herzinger et al.

(10) Patent No.: US 8,705,032 B2
(45) Date of Patent: Apr. 22, 2014

(54) TERAHERTZ-INFRARED ELLIPSOMETER SYSTEM, AND METHOD OF USE

(71) Applicants: Craig M. Herzinger, Lincoln, NE (US); Mathias M. Schubert, Lincoln, NE (US); Tino Hofmann, Lincoln, NE (US); Martin M. Liphardt, Lincoln, NE (US); John A. Woollam, Lincoln, NE (US)

(72) Inventors: Craig M. Herzinger, Lincoln, NE (US); Mathias M. Schubert, Lincoln, NE (US); Tino Hofmann, Lincoln, NE (US); Martin M. Liphardt, Lincoln, NE (US); John A. Woollam, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 0 days.

(21) Appl. No.: 13/815,487

(22) Filed: Mar. 7, 2013

(65) Prior Publication Data

US 2014/0027644 A1 Jan. 30, 2014

Related U.S. Application Data

(60) Division of application No. 12/802,638, filed on Jun. 11, 2010, now Pat. No. 8,416,408, which is a continuation-in-part of application No. 12/456,791, filed on Jun. 23, 2009, now Pat. No. 8,169,611, application No. 13/815,487, which is a continuation-in-part of application No. 13/506,848, filed on May 21, 2012, which is a continuation-in-part of application No. 12/802,734, filed on Jun. 14, 2010, now Pat. No. 8,488,119, which is a continuation-in-part of application No. 12/802,638, filed on Jun. 11, 2010, now Pat. No. 8,416,408, application No. 13/506,848, which is a continuation-in-part of application No. 12/456,791, filed on Jun. 23, 2009, now Pat. No. 8,169,611.

(60) Provisional application No. 61/281,905, filed on Nov. 22, 2009, provisional application No. 61/208,735, filed on Feb. 27, 2009.

(51) Int. Cl.
*G01J 4/00* (2006.01)

(52) U.S. Cl.
USPC .......................................... 356/364; 356/369

(58) Field of Classification Search
CPC .............. G01J 4/00; G01J 4/04; G01N 21/21
USPC .................................... 356/364, 369
See application file for complete search history.

(56) References Cited

U.S. PATENT DOCUMENTS

| | | | |
|---|---|---|---|
| 2,880,355 A | 3/1959 | Epsztein | 315/3.5 |
| 2,985,790 A | 5/1961 | Kompfner | 315/3.5 |

(Continued)

OTHER PUBLICATIONS

Distributed Photomixer, Ph.D. Thesis, Duen, MIT, Sep. 2002.

(Continued)

*Primary Examiner* — Roy M Punnoose
(74) *Attorney, Agent, or Firm* — James D. Welch

(57) ABSTRACT

The present invention relates to ellipsometer and polarimeter systems, and more particularly is an ellipsometer or polarimeter or the like system which operates in a frequency range between 300 GHz or lower and extending to higher than at least 1 Tera-hertz (THz), and preferably through the Infra-red (IR) range up to, and higher than 100 THz, including:
- a source such as a backward wave oscillator; a Smith-Purcell cell; a free electron laser, or an FTIR source and a solid state device; and
- a detector such as a Golay cell; a bolometer or a solid state detector;

and preferably including a polarization state generator comprising:
- an odd bounce image rotating system and a polarizer, or two polarizers;

and optionally including least one compensator and/or modulator, in addition to an analyzer.

21 Claims, 9 Drawing Sheets

(56) References Cited

U.S. PATENT DOCUMENTS

| | | | |
|---|---|---|---|
| 4,210,401 A * | 7/1980 | Batten | 356/369 |
| 4,332,476 A | 6/1982 | Stenberg et al. | 356/369 |
| 4,355,903 A | 10/1982 | Sandercock | 356/632 |
| 4,373,817 A | 2/1983 | Coates et al. | 356/636 |
| 4,647,207 A | 3/1987 | Bjork et al. | 356/369 |
| 4,750,822 A | 6/1988 | Rosencwaig et al. | 356/445 |
| 4,826,321 A | 5/1989 | Coates et al. | 356/492 |
| 4,838,695 A | 6/1989 | Mansuripur et al. | 356/369 |
| 5,042,951 A | 8/1991 | Gold et al. | 356/369 |
| 5,045,704 A | 9/1991 | Coates | 250/372 |
| 5,317,618 A | 5/1994 | Nakahara et al. | 378/161 |
| RE34,783 E | 11/1994 | Coates et al. | 250/372 |
| 5,373,359 A | 12/1994 | Woollam et al. | 356/328 |
| 5,452,091 A | 9/1995 | Johnson | 356/445 |
| 5,504,582 A | 4/1996 | Johs et al. | 356/369 |
| 5,521,706 A | 5/1996 | Green et al. | 356/369 |
| 5,596,406 A | 1/1997 | Rosencwaig et al. | 356/327 |
| 5,666,201 A | 9/1997 | Johs et al. | 356/369 |
| 5,706,212 A | 1/1998 | Thompson et al. | 702/85 |
| 5,757,494 A | 5/1998 | Green et al. | 356/369 |
| 5,872,630 A | 2/1999 | Johs et al. | 356/369 |
| 5,914,492 A | 6/1999 | Wang et al. | 250/397 |
| 5,946,098 A | 8/1999 | Johs et al. | 356/364 |
| 5,956,145 A | 9/1999 | Green et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,084,675 A | 7/2000 | Herzinger et al. | 359/369 |
| 6,100,981 A | 8/2000 | Johs et al. | 356/364 |
| 6,118,537 A | 9/2000 | Johs et al. | 356/369 |
| 6,137,618 A | 10/2000 | Herzinger | 359/369 |
| 6,141,102 A | 10/2000 | Johs et al. | 356/364 |
| 6,268,917 B1 | 7/2001 | Johs | 356/369 |
| 6,795,184 B1 | 9/2004 | Herzinger et al. | 356/369 |
| 6,798,511 B1 | 9/2004 | Zahn et al. | |
| 6,819,423 B2 | 11/2004 | Stehle et al. | 356/369 |
| 6,847,448 B2 | 1/2005 | Nagashima et al. | 356/364 |
| 7,274,450 B1 | 9/2007 | Green et al. | |
| 7,339,718 B1 | 3/2008 | Vodopanov et al. | 359/326 |
| 7,450,231 B2 | 11/2008 | Johs et al. | 356/365 |
| 7,460,230 B2 | 12/2008 | Johs et al. | 356/365 |
| 8,169,611 B2 * | 5/2012 | Herzinger et al. | 356/364 |
| 2003/0016358 A1 | 1/2003 | Nagashima et al. | |
| 2004/0027571 A1 | 2/2004 | Luttmann | |
| 2004/0228371 A1 | 11/2004 | Kolodzey et al. | |
| 2005/0175507 A1 | 8/2005 | Tsukruk | |
| 2006/0050269 A1 | 3/2006 | Brownell | |
| 2006/0068513 A1 | 3/2006 | Funakubo et al. | |
| 2006/0289761 A1 | 12/2006 | Nabet et al. | |
| 2007/0097373 A1 | 5/2007 | Pfeiffer et al. | |
| 2007/0252992 A1 | 11/2007 | Itsuji | |
| 2007/0278407 A1 | 12/2007 | Wood et al. | |

OTHER PUBLICATIONS

Hole Diffusion Profile in a P-P+Silicon Homojunction Determined by Terahertz & Infrared Spectroscopic Ellipsometry, Hofmann et al., App. Phys. Lett. 95 032102, (2009).

A review paper by Collins, titled "Automatic Rotating Element Ellipsometers: Calibration, Operation and Real-Time Applications", Rev. Sci. Instrum., 61(8) (1990).

An article titled "Gain of a Smith-Purcell Free Electron Laser", Andrews et al., Phy. Rev., vol. 7, 070701 (2004), describes use of Smith-Purcell Free Electron Laser.

"Terahertz Generalized Meuller-matrix Ellisometery", Hofmann et al., Proc. of SPIE, vol. 6120, pp. 61200D1-61200D10, (2005), describes applying Thz electromagnetic radiation in generalized ellipsometry wherein the source of the Thz electronmagnetic radiation is a synchrotron located at BESSY, in Germany.

"Terahertz magneto-optic generalized ellipsometry using synchrotron and blackbody radiation", Hofmann et al., American Inst. of Physics, 77, 063902-1 through 063902-12, (2006), describes applying Thz electromagnetic radiation in generalized ellipsometry wherein the source of the Thz electromagnetic radiation is a synchrotron and a conventional blackbody. The use of an FTIR source and bolometer is also mentioned.

"Label-free Amplified Bioaffinity Detection Using Terahertz Wave Technology", Menikh et al., Biosensors and Bioelectronics 20, 658-662 (2004), describes use of an unbiased GaAs crystal THz source of electromagnetic radiation and a ZnTe crystal detector.

Spectroscopy by Pulsed Terahertz Radiation, Hango et al., Meas. Sci. and Technol., 13 (2002), pp. 1727-1738, describes applying 30 GHz-10 THz and describes use of Fourier Transform Spectrometers (FTS) in the Far Infrared (FIR) frequency range with the caution that such an approach is not easily applied below 1 THz. Said reference also describes application of Backward Wave Oscillators (BWO) plus frequency multipliers, with the caution that to cover the range of 30 GHz to 3 THz typically requires many BWO's and frequency multipliers to cover said frequency range. This article favors use of a Femto-sec laser (eg. a mode-locked Ti:saphire laser or Er-doped fiber laser in combination with a photoconductive antenna made on low-temperature grown GaAs).

"Measurement of Complex Optical Constants of a Highly Doped Si Wafer Using Terahertz Ellipsometry", Nagashima et al., Applied Phys. Lett. vol. 79, No. 24 (Dec. 10, 2001). This article describes use of a mode-locked Ti:saphire laser with a bow-tie antenna and GaAs detector antenna).

"Development of Terahertz Ellipsometry and its Application to Evaluation of Semiconductors", Nagashima et al., Tech. Meeting on Light Application and Visual Science, IEEE (2002) proposed a Terahertz ellipsometer.

Terahertz Imaging System Based on a Backward-Wave Oscillator, Dobroiu et al., Applied Optics, vol. 43, No. 30, (Oct. 20, 2004) descirbes use of a Terahertz source to provide electromagnetic radiation.

A paper by Johs, titled "Regression Calibration Method for Rotating Element Ellipsometers", Thin Solid Films, 234 (1993) is also disclosed as it describes a mathematical regression based approach to calibrating ellipsometer systems.

"THz Ellipsometry in Theory and Experiment", Dietz et al. 33rd International Conference on Infrared and Millimeter Waves and 16th International Conference on Terahertz Electronics, IRMMW-THz (2008) describes an experimental ellipsometer for use in the THz frequency range.

"Study Terahertz Ellipsometry Setups for Measuring Metals and Dielectrics Using Free Electron Laser Light Source", Rudych, 31st International Conference on Infrared and Millimeter Waves and 14th International Conference on Terahertz Electronics, IRMMW-THz (2006) descibes use of a free electron laser to provide THz frequencies.

"Spectral THz Ellipsometer for the Unambiguous Determination of all Stokess Parameters", Holldack et al., 30th International Conference on Infrared and Millimeter Waves and 13th International Conference on Terahertz Electronics, IRMMW-THz (2006) describes a concept for determining all Stokes Parameters.

"Terahertz Magneto-Optic Generalized Ellipsometry Using Synchrotron and Blackbody Radiation", Esquinazi et al., Sci. Instrum., vol. 7, No. 6 (2006) describes use of synchrotron generated electromagentic radiation in magneto-optic generalized ellipsometry.

"Terahertz Generalized Mueller-Matrix Ellisometry", Esquinazi et al. Proc. Int. Soc. Opt. Eng., vol. 6120, (2006) describes synchrotron generated electromagentic radiation in generalized Mueller Matrix ellipsometry.

"THz Time-Domain Magneto-Optic Ellipsometry in Reflection Geometry", Kuwata-Gonokami et al., Trends Opt. Photonics Series, vol. 97, (2004) describes determining a dielectric tensor using THz frequencies in magneto-optic optical measurements.

"Terahertz Polarimetry", Gallot et al., Conf. Lasers Electro-Optics, CLEO, vol. 3 (2005) describes determining the polarization state of a THz wave over a wide rnge of frequencies.

"Evalution of Complex Optical Constants of Semiconductor Wafers using Terahertz Ellipsometry", Hangyo et al., Trends Opt. Photonics Series, vol. 88, (2003) descris combining terahertz ellipsometry with time domain spectroscopy.

(56) References Cited

OTHER PUBLICATIONS

"Improved Performance of Hybrid Electronic Terahertz Generators", Hurlbut et al., 33rd International Conference on Infrared and Millimeter Waves and Terahertz Waves, IRMMW-THz (2008), describes combining BWO's with frequency multipliers.

"Terahertz Wave Generation in Orientation-Patterned GaAs Using Resonantly Enhanced Schemes", Vodopyanov et al., SPIE—Intl. Soc. for Opt. Eng. USA, vol. 6455, (2007), describs application of Zincblende semiconductors (GaAs, GaP) to produce THz frequencies.

"Terahertz BWO Spectroscopy of Conductors and Superconductors", Gorshunov et al., Quantum Electronics, vol. 37, No. 10 (Oct. 2007), describes methods for directly measuring dielectric response spectra of dielectrics, consuctors and superconductors using BWO generated spectrometers.

"Portable THz Spectrometers", Kozlov et al., 31st International Conference on Infrared and Millimeter Waves and 14th International Conference on Terahertz Electronics, IRMMW-THz (2007), decribes a portable THz spectrometer which operates in the frequency range of 0.1-1 THz.

"Terahertz Time-Domain Spectrsocopy", Nishizawa et al., Terahertz Optoelectronics, Topics Appl. Phys. 97, 203-271 (2005).

\* cited by examiner

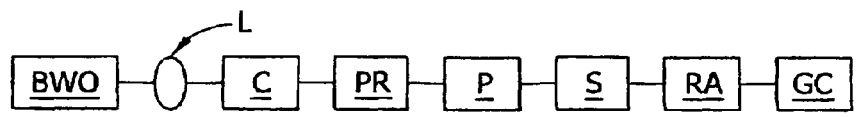
FIG. 1_L
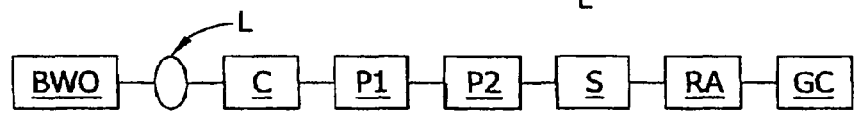
FIG. 1_M
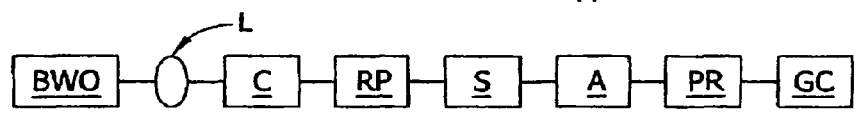
FIG. 1_N
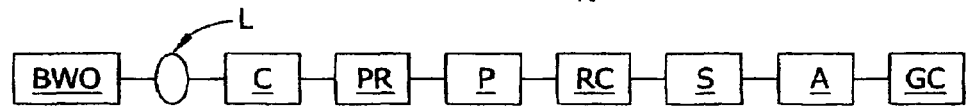
FIG. 1_O
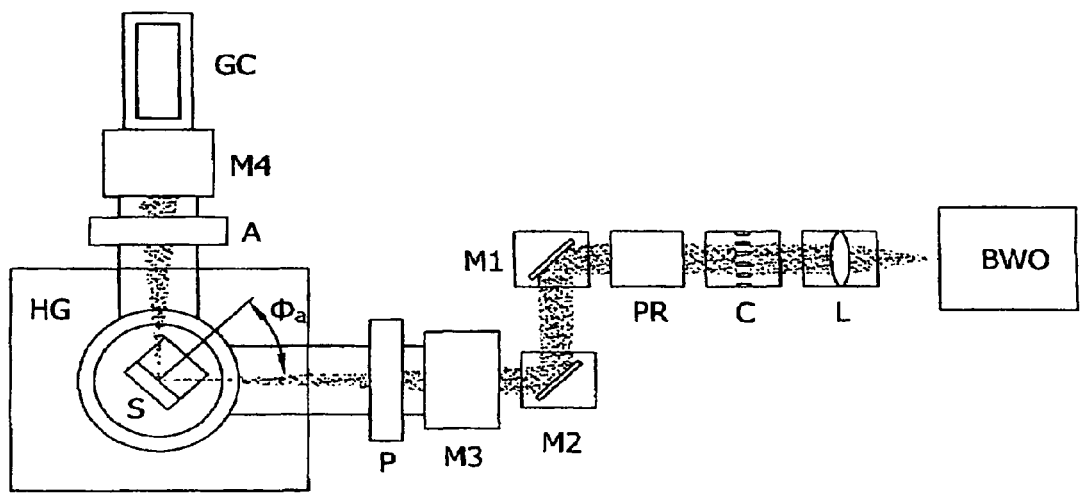
FIG. 1_P

TERAHERTZ-INFRARED ELLIPSOMETER SYSTEM, AND METHOD OF USE

CROSS-REFERENCE TO OTHER APPLICATIONS

This Application is a Divisional of Ser. No. 12/802,638 Filed Jun. 11, 2010, and therevia is a CIP of Ser. No. 12/456,791 Filed Jun. 23, 2009 and therevia Claims Benefit of Provisional Application Ser. No. 61/208,735 Filed Feb. 27, 2009, and further Claims Benefit of Provisional Application Ser. No. 61/281,905 Filed Nov. 22, 2009.

STATEMENT OF FINANCIAL SUPPORT

This invention which is subject in this application was developed in part under support provided by a Grant from the Army under Phase I ARMY STTR Contract No. W911NF-08-C-01121.

The portion of this invention concerning the "odd bounce image rotation system and method of use" in this application was developed in part under support provided by a Grant from the National Science Foundation under Phase II SBIR Contract No. 9901510.

The United States Government has certain rights in this invention.

TECHNICAL FIELD

The present invention relates to ellipsometer and polarimeter systems which comprise a source of electromagnetic radiation, a polarization state generator, a sample supporting stage, a polarization state detector and a detector of electromagnetic radiation, and more particularly is an ellipsometer or polarimeter or the like system which operates in a frequency range between 300 GHz or lower and extending to higher than at least 1 Tera-hertz (THz), and preferably through the Infra-red (IR) range up to, and higher than 100 THz, comprising:
   a source such as a backward wave oscillator; a Smith-Purcell cell; a free electron laser, an FTIR source and/or a solid state device; and
   a detector such as a Golay cell; a bolometer and/or a solid state detector;
preferably in functional combination with a polarization state image rotating system comprised of a sequence of an odd number of reflecting elements, such that a polarized electromagnetic beam caused to enter, reflectively interacts with the odd number of reflecting elements and exits in a direction which is essentially non-deviated and non-displaced, with an azimuthally rotated, but otherwise substantially unchanged, polarization state.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

Before proceeding, as it is relevant to the present invention, it is noted that ellipsometer systems generally comprise means for setting a linear or elliptical polarization state, (typically substantially linear).

Continuing, in general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system. The governing equation is:

$$\rho = rp/rs = \text{Tan}(\Psi)\exp(i\Delta)$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:
   a. a Source of a beam electromagnetic radiation;
   b. a Polarizer element;
   c. optionally a compensator element;
   d. (additional element(s));
   e. a sample system;
   f. (additional element(s));
   g. optionally a compensator element;
   h. an Analyzer element; and
   i. a Spectroscopic Detector System.

Each of said components b.-i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. It is noted, that nulling ellipsometers also exist in which elements therein are rotatable in use, rather than rotating. Generally, use of a nulling ellipsometer system involves imposing a substantially linear polarization state on a beam of electromagnetic radiation with a linear polarizer, causing the resulting polarized beam of electromagnetic radiation to interact with a sample system, and then adjusting an analyzer to an azimuthal angle which effectively cancels out the beam of electromagnetic radiation which proceeds past the sample system. The azimuthal angle of the analyzer at which nulling occurs provides insight to properties of the sample system.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow calibration of ellipsometers and evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Before disclosing known references, it is noted that computer searching at the PTO Website for Patents and Published Applications containing the words:
 (ellipsometer & bolometer); and
 (ellipsometer & Golay cell);
produced only one hit, that being Published Application US2005/0175507 by Tsukruk. Said 507 reference does contain the words ellipsometry and Golay, but does not describe an ellipsometer system comprising said elements.

Further, a PTO Website Search for Patents and Published Applications containing the words:
 (ellipsometer & backward wave oscillator);
 (ellipsometer & Smith-Purcell); and
 (ellipsometer & free electron laser);
produced only U.S. Pat. No. 5,317,618 to Nakahara et al., which contains the words ellipsometer & free electron laser, but does not describe a combination of said elements.

A Patent to Wang et al., U.S. Pat. No. 5,914,492 is of interest as it describes free electron lasers used in combination with a Golay cell and Smith-Purcell detectors. However, it does not describe application in ellipsometry or polarimetry.

A Published Application, US2006/0050269 by Brownell describes use of a free electron laser and a Smith-Purcell detector, but not in the context of ellipsometry or polarimetry.

An article titled "Gain of a Smith-Purcell Free Electron Laser", Andrews et al., Phy. Rev., Vol 7, 070701 (2004), describes use of Smith-Purcell Free Electron Laser.

U.S. Pat. No. 2,985,790 to Kompfner is disclosed as it describes a Backward Wave Oscillator.

U.S. Pat. No. 2,880,355 to Epsztein is disclosed as it describes a Backward Wave Oscillator.

Known References which describe Ellipsometers which operate in the THz frequency range are:
 "Terahertz Generalized Meuller-matrix Ellipsometery", Hofmann et al., Proc. of SPIE, Vol. 6120, pp. 61200D1-61200D10, (2005), describes applying Thz electromagnetic radiation in generalized ellipsometry wherein the source of the Thz electromagnetic radiation is a synchrotron located at BESSY, in Germany.
 "Terahertz magneto-optic generalized ellipsometry using synchrotron and blackbody radiation", Hofmann et al., American Inst. of Physics, 77, 063902-1 through 063902-12, (2006), describes applying Thz electromagnetic radiation in generalized ellipsometry wherein the source of the Thz electromagnetic radiation is a synchrotron and a conventional blackbody. The use of an FTIR source and bolometer is also mentioned.
 "Label-free Amplified Bioaffinity Detection Using Terahertz Wave Technology", Menikh et al., Biosensors and Bioelectronics 20, 658-662 (2004), describes use of an unbiased GaAs crystal THz source of electromagnetic radiation and a ZnTe crystal detector.
 Spectroscopy by Pulsed Terahertz Radiation", Hango et al., Meas. Sci. and Technol., 13 (2002), pp 1727-1738, describes applying 30 GHz-10 THz and describes use of Fourier Transform Spectrometers (FTS) in the Far Infrared (FIR) frequency range with the caution that such an approach is not easily applied below 1 THz. Said reference also describes application of Backward Wave Oscillators (BWO) plus frequency multipliers, with the caution that to cover the range of 30 GHz to 3 THz typically requires many BWO's and frequency multipliers to cover said frequency range. This article favors use of a Femto-sec laser (eg. a mode-locked Ti:sapphire laser or Er-doped fiber laser in combination with a photoconductive antenna made on low-temperature grown GaAs).
 "Measurement of Complex Optical Constants of a Highly Doped Si Wafer Using Terahertz Ellipsometry", Nagashima et al., Applied Phys. Lett. Vol. 79, No. 24 (10 Dec. 2001). This article describes use of a mode-locked Ti:sapphire laser with a bow-tie antenna and GaAs detector antenna).
 Published Patent Application No. US2004/0027571 by Luttman mentions using a THz light Source in an ellipsometer system.
 "Development of Terahertz Ellipsometry and its Application to Evaluation of Semiconductors", Nagashima et al., Tech. Meeting on Light Application and Visual Science, IEEE (2002) proposes a Terahertz ellipsometer.
 "Terahertz Imaging System Based on a Backward-Wave Oscillator, Dobroiu et al., Applied Optics, Vol. 43, No 30, (20 Oct. 2004) describes use of a Terahertz source to provide electromagnetic radiation.
 A Patent to Herzinger et al. U.S. Pat. No. 6,795,184, describes an "Odd-Bounce" system for rotating a polarization state in an electromagnetic beam. Patents disclosed in the Application leading to U.S. Pat. No. 6,795,184 are:
 Patent to Herzinger, U.S. Pat. No. 6,137,618 is disclosed as it describes a Single Brewster Angle Polarizer in the context of multiple reflecting means, and discloses prior art dual Brewster Angle Single Reflective Means Polarizer Systems.
 Patent, to Herzinger et al., U.S. Pat. No. 6,084,675 describes an adjustable beam alignment compensator/retarder with application to spectroscopic ellipsometry.
 U.S. Pat. No. 6,118,537 to Johs et al. describes a multiple Berek plate optical retarder system.
 U.S. Pat. No. 6,141,102 to Johs et al. describes a single triangular shaped optical retarder element.
 U.S. Pat. No. 5,946,098 to Johs et al., describes dual tipped wire grid polarizers in combination with various compensator/retarder systems.
 U.S. Pat. No. 6,100,981 to Johs et al., describes a dual horizontally oriented triangular shaped optical retarder.
 U.S. Pat. No. 6,084,674 to Johs et al., describes a parallelogram shaped optical retarder element.
 U.S. Pat. No. 5,963,325 to Johs et al., describes a dual vertically oriented triangular shaped optical retarder element.
 U.S. Pat. Nos. 7,450,231 and 7,460,230 to Johs et al. are disclosed as they describe deviation angle self compensating compensator systems.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

Further Patents disclosed in the 184 Patent are:

U.S. Pat. Nos. 5,757,494; and 5,956,145;
to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

Patents of general interest disclosed in the 184 Patent include:

Patent to Woollam et al, U.S. Pat. No. 5,373,359, (describes a beam chopper);
Patent to Johs et al. U.S. Pat. No. 5,666,201;
Patent to Green et al., U.S. Pat. No. 5,521,706; and
Patent to Johs et al., U.S. Pat. No. 5,504,582;
and are disclosed as they pertain to ellipsometer systems.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are:

No. RE 34,783,
U.S. Pat. No. 4,373,817,
U.S. Pat. No. 5,045,704
    to Coates; and
U.S. Pat. No. 5,452,091
    to Johnson.

A Patent to Biork et al., U.S. Pat. No. 4,647,207 is disclosed as it describes an ellipsometer system which has provision for sequentially, individually positioning a plurality of reflective polarization state modifiers in a beam of electromagnetic radiation. U.S. Pat. Nos. 4,210,401; 4,332,476 and 4,355,903 are also identified as being cited in the 207 patent. It is noted that systems as disclosed in these patents, (particularly in the 476 Patent), which utilize reflection from an element to modify a polarization state can, if such an element is an essential duplicate of an investigated sample and is rotated ninety degrees therefrom, the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,596,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

In addition to the identified Patents, certain Scientific papers were also disclosed in the 184 Patent are:

A paper by Johs, titled "Regression Calibration Method for Rotating Element Ellipsometers", Thin Solid Films, 234 (1993) is also disclosed as it describes a mathematical regression based approach to calibrating ellipsometer systems.

An additional relevant Patent is U.S. Pat. No. 6,268,917 to Johs. This patent describes a combined polychromatic electromagnetic radiation beam source comprising beam combiners.

It is also disclosed that the J. A. Woollman Co., Inc. has marketed an IR range Ellipsometer, called the IR-VASE®, for many years. Said instrument provides capability from 10 THz to 150 THz and is a Variable Angle, Rotating Compensator system utilizing a Bomen FTIR Spectrometer. Further, it comprises an FTIR Source, and an Odd-Bounce image rotating system for rotating a polarization state imposed by a wire-grid polarizer. It is noted that as marketed, this system has never provided the capability to reach down to 1 THz, which capability was achieved via research in developing the present invention.

Additional references which describe ellipsometry practiced in the THz range are:

"THz Ellipsometry in Theory and Experiment", Dietz et al. 33rd International Conference on Infrared and Millimeter Waves and 16th International Conference on Terahertz Electronics, IRMMW-THz (2008) describes an experimental ellipsometer for use in the THz frequency range;

"Study Terahertz Ellipsometry Setups for Measuring Metals and Dielectrics Using Free Electron Laser Light Source", Rudych, 31st International Conference on Infrared and Millimeter Waves and 14th International Conference on Terahertz Electronics, IRMMW-THz (2006) describes use of a free electron laser to provide THz frequencies;

"Spectral THz Ellipsometer for the Unambiguous Determination of all Stokess Parameters", Holldack et al., 30th International Conference on Infrared and Millimeter Waves and 13th International Conference on Terahertz Electronics, IRMMW-THz (2006) describes a concept for determining all Stokes Parameters;

"Terahertz Magneto-Optic Generalized Ellipsometry Using Synchrotron and Blackbody Radiation", Esquinazi et al., Sci. Instrum., Vol. 7, No. 6 (2006) describes use of synchrotron generated electromagnetic radiation in magneto-optic generalized ellipsometry;

"Terahertz Generalized Mueller-Matrix Ellisometry", Esquinazi et al. Proc. Int. Soc. Opt. Eng., Vol. 6120, (2006) describes synchrotron generated electromagnetic radiation in generalized Mueller Matrix ellipsometry "THz Time-Domain Magneto-Optic Ellipsometry in Reflection Geometry", Kuwata-Gonokami et al., Trends Opt. Photonics Series, Vol. 97, (2004) describes determining a dielectric tensor using THz frequencies in magneto-optic optical measurements;

"Terahertz Polarimetry", Gallot et al., Conf. Lasers Electro-Optics, CLEO, Vol. 3 (2005) describes determining the polarization state of a THz wave over a wide range of frequencies;

"Evaluation of Complex Optical Constants of Semiconductor Wafers using Terahertz Ellipsometry", Hangyo et al., Trends Opt. Photonics Series, Vol. 88, (2003) describes combining terahertz ellipsometry with time domain spectroscopy.

Additional references which describe sources of Terahertz frequency range electromagnetism are:

"Improved Performance of Hybrid Electronic Terahertz Generators", Hurlbut et al., 33rd International Conference on Infrared and Millimeter Waves and Terahertz Waves, IRMMW-THz (2008), describes combining BWO's with frequency multipliers;

"Terahertz Wave Generation in Orientation-Patterned GaAs Using Resonantly Enhanced Schemes", Vodopyanov et al., SPIE-Intl. Soc. for Opt. Eng. USA, Vol. 6455, (2007), describes application of Zincblende semiconductors (GaAs, GaP) to produce THz frequencies;

"Terahertz BWO Spectroscopy of Conductors and Superconductors", Gorshunov et al., Quantum Electronics, Vol. 37, No. 10 (October 2007), describes methods for directly measuring dielectric response spectra of dielectrics, conductors and superconductors using BWO generated spectrometers;

"Portable THz Spectrometers", Kozlov et al., 31st International Conference on Infrared and Millimeter Waves and 14th International Conference on Terahertz Electronics, IRMMW-THz (2007), describes a portable THz spectrometer which operates in the frequency range of 0.1-1 THz;

"Terahertz Time-Domain Spectroscopy", Nishizawa et al., Terahertz Optoelectronics, Topics Appl. Phys. 97, 203-271 (2005).

U.S. Pat. No. 7,339,718 to Vodopanov et al., Issued Apr. 3, 2008 describes a method for generating THz radiation comprising illuminating a semiconductor with an optical pulse train.

U.S. Pat. No. 6,819,423 to Stehle et al., Issued Nov. 16, 2004 and U.S. Pat. No. 5,317,618 Issued Jan. 25, 2005 are also identified as they mention application of THz frequencies in an ellipsometer system.

It is noted that the Search Report for a co-pending PCT Application, PCT/US09/05346, was recently received. It identified the following references: U.S. Pat. Nos. 6,795,184; 7,274,450 and 6,798,511; and Published Applications Nos. US2004/0228371; US2007/0252992; US2006/0289761; US2007/0278407; US2007/0097373. Also identified were: a Ph.D. dissertation by Duerr, Erik Kurt, titled "Distributed Photomixers", Mass. Inst. Tech., September 2002; and article titled "Hole Diffusion Profile in a P-P+ Silicon Homojunction Determined by Terahertz and Midinfrared Spectroscopic Ellipsometry", Hofmann et al., App. Phys. Lett., 95 032102 (2009).

The identified references, application Ser. No. 12/456,791, Provisional Application Ser. No. 61/208,735 and Ser. No. 61/281,905, are all incorporated by reference into this Specification.

Even in view of relevant prior art, there remains need for an ellipsometer or polarimeter system for application in the Terahertz region, preferably in combination with a convenient approach to providing linearly polarized beams of electromagnetic radiation in which the azimuthal angle of the linear polarization can be controlled.

DISCLOSURE OF THE INVENTION

As disclosed in a Co-Pending Parent application Ser. No. 12/456,791, the present invention is a practical ellipsometer or polarimeter system for application in the range of frequencies between 300 GHz or below and proceeding well into and preferably through the Infrared frequency range. The prior art demonstrates that it is not unknown to propose, or provide a system for, and practice of ellipsometry at Terahertz (THz) frequencies, however, a specific embodiment than makes such possible and which is suitable for general application in universities and industry etc., has not been previously disclosed. To the Applicant's knowledge, there are no commercially available THz ellipsometers or polarimeters available in the market place. This is even more so the case where the ellipsometer or polarimeter also provides Infrared (IR) frequency capability.

While Synchrotrons have been used to provide THz frequency band electromagnetic radiation in ellipsometers, it is not remotely possible to provide a Synchrotron at every location whereat it is desired to practice THz ellipsometry. The present invention provides combination of many elements, which results in a novel, practical system for general application in the market place.

Before proceeding, it is of benefit to define some terminology. First, a generally accepted range for what constitutes a Terahertz range of frequencies is from $3\times10^{11}$ (ie. 300 GHz), to $1.3\times10^{12}$ (ie. 1.3 Thz), Hertz. The Terahertz range is sandwiched between the microwave, (the high end of which has a wavelength of 1 millimeter), and the far-infrared, (the long-wavelength edge of which is 100 micrometers), ranges of wavelengths/frequencies.

Next, it is noted that a number of sources of Terahertz (THz) electromagnetic radiation exit. For instance, a Smith-Purcell cell is a device which directs an energetic beam of electrons very close to a ruled surface of a diffraction grating. The effect on the trajectory of the beam is negligible, but a result is that Cherenkov radiation in the Terahertz frequency range can be created, where the phase velocity of the electromagnetic radiation is altered by the periodic grating. Another source of Terahertz radiation is a Free Electron Laser. In this source a beam of electrons is accelerated to relativistic speed and caused to pass through a periodic transverse magnetic field. The array of magnets is sometimes called an undulator or "wiggler" as it causes the electrons to form a sinusoidal path. The acceleration of the electrons causes release of photons, which is "synchrotron radiation". Further, the electron motion is in phase with the field of said released electromagnetic radiation, and therefore the fields add coherently. Instabilities in the electron beam resulting from interactions of the oscillations in the undulators lead to emission of electromagnetic radiation, wherein electrons radiate independently. The wavelength of the emitted electromagnetic radiation from the electrons can be adjusted by adjusting the energy of the electron beam and/or magnetic field strength of the undulators, to be in the Terahertz range. Another source of Terahertz frequencies is a Backward Wave Oscillator (BWO), which is a vacuum tube system comprising an electron gun that generates an electron beam and causes it to interact with an electromagnetic wave traveling in a direction opposite to that of ejected electrons such that THz frequency oscillations are sustained by interaction between the propagating traveling wave backwards against the electron beam.

It is also disclosed that numerous detectors exist for monitoring Terahertz range electromagnetic radiation. One example is a Golay cell which operates by converting a temperature change resulting from electromagnetic radiation impinging onto material, into a measurable signal. Generally, when electromagnetic radiation is caused to impinge on a blackened material it heats a gas, (eg. Xenon) in an first chamber of an enclosure, and that causes a distortable reflecting diaphragm/film adjacent to said first chamber to change shape. In a second chamber, separated from the first by said diaphragm/film an electromagnetic beam is caused to reflect from the film and into a photocell, which in turn converts the received electromagnetic radiation into an electrical signal. A Bolometer is another detector of monitoring Terahertz range electromagnetic radiation, but operates by using the effect of a changing electric resistance caused by electromagnetic radiation impinging onto a blackened metal.

It is also noted that there are Solid State sources and detectors of Terahertz frequency electromagnetic radiation. For instance, an identified reference by Nagashima et al. discloses that THz pulses can be generated by a bow-tie photoconductive radiation antenna excited by a mode-locked Ti-sapphire laser with 80 Fs time width pulses, and a detection antenna can be formed from a dipole-type photoconductive antenna with a 5 micron gap fabricated on thin film LT-GaAs. Further, it is known that a company named AB Millimeter in Paris France, supplies a system that covers the entire range from 8 GHz to 1000 GHz with solid state source and detector devices.

With the above insight, it is disclosed that the present invention comprises an ellipsometer or polarimeter system which comprises a selection from the group consisting of:
- a1) a source of electromagnetic radiation in functional combination with a polarization state generator that provides substantially polarized output in a frequency range between 300 GHz or lower and extending higher than at least 1 THz;
- a2) a polarization state generator comprising a THz source of electromagnetic radiation that provides substantially polarized output in a frequency range between 300 GHz or lower and extending higher than at least 1 THz;
- b) a sample support;
- c) at least one detector of electromagnetic radiation, said at least one detector being capable of detecting electromagnetic radiation in a range of between 300 GHz or lower and extending higher than at least 1 THz.

Said ellipsometer or polarizer system further comprises, between said THz source and said detector, at least one selection from the group:
- a stationary, rotatable or rotating polarizer between said THz source and said sample support;
- a stationary, rotatable or rotating analyzer between said sample support and said detector;
- a stationary, rotatable or rotating compensator between said source and detector; and
- an electro, acousto or opto-modulator;

the purpose thereof being to modulate a polarization state during a data acquisition procedure.

It is noted that the polarization state generator comprising a THz source of electromagnetic radiation that provides substantially polarized output in a frequency range between 300 GHz or lower and extending higher than at least 1 THz, utilizes natural-polarization provided by the THz source and does not require use of a separate polarizer; whereas said source of electromagnetic radiation in functional combination with a polarization state generator that provides substantially polarized output in a frequency range between 300 GHz or lower and extending higher than at least 1 THz, typically comprises a separate polarizer.

Continuing, the THz source of electromagnetic radiation can comprise at least one selection from the group consisting of:
- a backward wave oscillator;
- a Smith-Purcell cell;
- a free electron laser; and
- a solid state source device;

and preferably further comprises a frequency multiplier means after said THz source of electromagnetic radiation, which frequency multiplier receives electromagnetic radiation output from said THz source, and provides harmonics of said electromagnetic radiation in a range of between said source output fundamental and about 1.6 THz.

Further, the ellipsometer or polarimeter system preferably comprises at least one odd-bounce polarization state rotation system present between:
- said THz source of electromagnetic radiation; and
- said detector;

and comprises a method of its application in ellipsometer and polarimeter and the like systems. This is beneficial in that it eliminates the need to rotate an ellipsometer system Polarizer to rotate a polarization state provided by the source of electromagnetic radiation, optionally in combination with a polarization state generator. The odd bounce optical image rotating system is disclosed in U.S. Pat. No. 6,795,184 to Herzinger et al. As described in said 184 Patent said odd bounce serves optical image rotating system serves to rotate the azimuthal angle of a linearly, or partially linearly polarized, (ie. substantially polarized), beam of electromagnetic radiation without entering significant deviation or displacement of the propagation direction locus thereof, or significantly altering the polarization state thereof, (ie. it does not cause significant shifting of energy from a major intensity orthogonal component into the other orthogonal component, or the shifting of phase angle therebetween). The odd bounce optical image rotating system can be described as a sequence of an odd number of reflective elements oriented in a manner which causes an entering beam of electromagnetic radiation to reflect from a first thereof onto the second thereof and from the second thereof onto the third thereof etc. For a three (3) reflective element odd bounce optical image rotating element system, said three reflections cause a beam of electromagnetic radiation to emerge from the third reflective element with a rotated linear or partially linear polarization azimuthal angle and in a direction which is not significantly deviated or displaced from the locus of the input beam, even when the odd bounce optical image rotating system is caused to stepwise or continuously rotate about an axis coincident with the locus of the beam of electromagnetic radiation. The same is generally true for an odd bounce optical image rotating element system comprising any odd number, (eg. 3, 5, 7 etc.) of reflective elements. It is noted that the greater the number of reflective elements the more normal the angle of incidence a beam can make thereto, and higher angles of incidence cause less aberration effects. Also, where more than three reflection elements are present certain non-idealities caused by the reflection elements can be canceled by utilizing non-coincident coordinate systems for said reflections. A trade-off, however, is that the greater the number of reflective elements present, the more difficult it is to align the system to avoid said beam deviation and displacement.

Coupling the odd bounce optical image rotating system with a substantially linear polarizing element, (which can comprise a source of unpolarized electromagnetic radiation and a polarizer, or can comprise a source that provides polarized electromagnetic radiation at its output), provides a polarizer system in which the polarizing element can remain stationary while the azimuthal angle of the polarized beam of electromagnetism exiting therefrom, (as viewed from a position along the locus of an electromagnetic beam caused to enter thereto), is rotated.

For general insight, it is also noted that a single three-hundred-sixty (360) degree rotation of a present invention odd bounce optical image rotating element system about an axis coincident with a beam of electromagnetic radiation which functionally passes therethrough, causes seven-hundred-twenty (720) degrees of rotation of the major intensity orthogonal component. This is not of any critical consequence, but is mentioned as it must be taken into account during practice of present invention methodology.

The detector of electromagnetic radiation in a range between 300 GHz or lower and extending higher than 1 THz, can be a selection from the group consisting of:
   a Golay cell;
   a bolometer
   a solid state detector.

Further, said ellipsometer or polarimeter system further comprises an FTIR source and a detector for detecting said FTIR frequency output in a frequency range above about 1 THz, and means for selecting between:
   said THz source of electromagnetic radiation and optional frequency multiplier that provides THz frequency output in a range between 300 GHz or lower and extending higher than at least 1 THz; and
   said FTIR source that provides output in an IR frequency range above about 1 THz.

The detector for detecting said FTIR frequency output in a frequency range above about 1 THz, and in which said detector of electromagnetic radiation in a range between 300 GHz or lower and extending higher than at least 1 THz, are each independently selected from the group:
   a Golay cell;
   a bolometer; and
   a solid state detector.

As mentioned, in a preferred embodiment, the ellipsometer or polarimeter system has output from said THz source, preferably with a frequency multiplier in functional combination, so that it overlaps output from said FTIR source in frequency, between at least 1.0 to 1.4 THz. And preferably said sources are calibrated such that substantially the same results, (eg. ellipsometric PSI and/or DELTA), are achieved by analyzing output from either of the selected detectors in the frequency range of between about 1.0 to 1.4 THz.

In more detail, a preferred present invention ellipsometer or polarimeter system comprises:
a selection from the group consisting of:
   a1) an FTIR source of electromagnetic radiation in functional combination with a polarization state generator, that provides substantially polarized output in a frequency range above about 1 THz; and
   a2) a polarization state generator comprising an FTIR source of electromagnetic radiation which provides substantially polarized output in a frequency range above about 1 THz;
and a selection from the group consisting of:
   a3) a THz source of electromagnetic radiation in functional combination with a polarization state generator, that provides substantially polarized output in a frequency range between 300 GHz or lower and extending higher than at least 1 THz;
   a4) a polarization state generator comprising a THz source of electromagnetic radiation that provides substantially polarized output in a frequency range between 300 GHz or lower and extending higher than at least 1 THz;
   wherein said THz source of electromagnetic radiation comprises at least one selection from the group consisting of:
      a backward wave oscillator;
      a Smith-Purcell cell;
      a free electron laser; and
      a solid state device;
   preferably in functional combination with a frequency multiplier for providing harmonics of a fundamental output frequency that provides substantially polarized frequency output in a frequency range between 300 GHz or lower and extending higher than at least 1 THz.
Further, said ellipsometer or polarimeter comprises means for selecting between said THz and FTIR sources.
   Said ellipsometer or polarimeter further comprises:
   b) a sample support;
   c) a detector system of electromagnetic radiation comprising at least one selection from the group consisting of:
      a Golay cell detector;
      a bolometer detector;
      a solid state source device.
Said preferred ellipsometer or polarization system embodiment further comprises at least one odd-bounce polarization state rotation system present between:
   said selected source; and
   said selected detector.
And, said ellipsometer system further comprises, between said selected source and said selected detector, at least one selection from the group:
   a stationary, rotatable or rotating polarizer between said THz source and said sample support;
   a stationary, rotatable or rotating analyzer between said sample support and said detector;
   a stationary, rotatable or rotating compensator between said source and detector; and
   an electro, acousto or opto-modulator.
   In use a selected functional combination of selected source and selected detector is applied to cause electromagnetic radiation to impinge on and interact with a sample on said sample support, then enter said selected detector, to the end that said detector produces an output.
Again, said preferred embodiment provides that the output from the functional combination of said selected THz source and preferably a frequency multiplier, and that from said FTIR source overlap in frequency between at least 1.0 to 1.4 THz such that substantially the same results, (eg. ellipsometric PSI and/or DELTA), are achieved by analyzing output from either of the selected detectors in the frequency range of between about 1.0 to 1.4 THz.

A preferred present invention system also comprises a chopper for chopping the electromagnetic beam which interacts with the sample. (It is noted that FTIR Sources provide a natural "chopping" effect by way of a moving mirror therewithin, hence, an added chopper is relevant only when a THZ Source is selected). Further, a chopper is typically applied when other elements are caused to rotate during data acquisition. Use of a chopper enables noise reduction, particularly where data is obtained with the system located in a non-darkened room, such that spurious electromagnetic radiation is present.

A present invention method of characterizing a sample comprises the steps of:

A) providing an ellipsometer or polarimeter as described above;

B) selecting a source and detector;

C) applying said selected source to cause substantially polarized electromagnetic radiation to impinge on and interact with said sample on said sample support, then proceed to and enter said selected detector, to the end that said detector provides output.

The present invention method also preferably involves chopping the substantially polarized electromagnetic radiation which is caused to impinge on and interact with said sample on said sample support, and which then proceeds to and enters said selected detector, to the end that said detector provides output based substantially only on the chopped beam content.

And, said method can further comprise performing at least one selection from the group consisting of:

storing at least some output provided by said detector in machine readable media;

analyzing at least some of the output provided by said detector and storing at least some of the results of said analysis in machine readable media;

displaying at least some output provided by said detector by electronic and/or non-electronic means;

analyzing at least some of the output provided by said detector and displaying at least some of the results of said analysis by electronic and/or non-electronic means;

causing at least some output provided by said detector to produce a signal which is applied to provide a concrete and tangible result;

analyzing at least some of the output provided by said detector and causing at least some thereof to produce a signal which is applied to provide a concrete and tangible result.

Said method can further comprise the step of continuously or step-wise rotating at least one of the at least one odd-bounce polarization state rotation system present between said source and detector, or operating a present electro, acousto or opto-modulator, during data acquisition.

The benefit is that, especially in ellipsometer/polarimeter etc. systems which operate in the IR range of wavelengths and below, it can be difficult to cause rotation of a linear polarizer, (or analyzer), without adversely causing deviation of a beam of electromagnetic radiation caused to pass therethrough, or causing mis-coordination of multiple elements thereof, (ie. multiple tipped wire linear polarizer as described in U.S. Pat. No. 5,946,098). The present invention allows setting fixed substantially linear polarizer, and analyzer azimuthal orientations, and using the odd bounce optical image rotating element instead, to effect different electromagnetic beam azimuthal rotation orientations.

It is also noted that various selected combinations of elements that comprise an ellipsometer or polarimeter, such as a specific selection from:

a backward wave oscillator;

a Smith-Purcell cell;

a free electron laser; and a solid state device;

preferably in functional combination with a frequency multiplier for providing harmonics of a fundamental output frequency that provides substantially polarized frequency output in a frequency range between 300 GHz or lower and extending higher than at least 1 THz;

and an FTIR Source;

in combination with selection from various types of Polarizers and Analyzers and/or Compensators, as well as the motion of each (ie. stationary, rotatable or rotating), and beam chopper frequency during data acquisition;

in further functional combination with a specific selection from:

a Golay cell detector;

a bolometer detector;

a solid state source device;

for each of the THz and IR ranges of operation, can provide different quality or, for instance, ellipsometric PSI or DELTA results, as quantified by measured Noise/Signal ratios, and extent of wavelength range. As regards the later point, it is noted that it can be advantageous to provide two THz sources which provide different wavelength output and combine their outputs.

At the time of this submittal it is believed that a preferred embodiment makes use of a backward wave oscillator (BWO) in combination with a multiplier that provides ×1, ×2 ×3 ×6 and ×9 capability, in functional combination with Golay cell or bolometer, provides good results in the range of from about 0.12-1.5 THz. Further, a conventional FTIR Source as used in a J. A. Woollam Co. IR-VASE®, to provide 10-150 THz capability, has been shown capable of providing output down to about 1.0 Thz. This beneficially allows an overlap between the THz and IR sources between about 1.0 and 1.4 Thz, which can be used for verification of results separately obtained using the THz and IR sources. In addition, it can be advantageous to cool a detector, (eg. by use of liquid helium), and to adjust beam chopper rate, (eg. between about 12-50 Hz), differently for different source and detector combinations.

It is further believed that a present invention ellipsometer or polarimeter system which comprises:

a2) a polarization state generator comprising a THz source of electromagnetic radiation that provides substantially polarized output in a frequency range between 300 GHz or lower and extending higher than at least 1 THz; and thereafter comprises at least one odd bounce optical image rotating system which comprises:

an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector;

is definitely new and Patentable; particularly when it further comprises at least two rotating elements, each thereof being selected from the group consisting of:

a rotating polarizer between said source and said sample supporting stage;

a rotating analyzer between said sample supporting stage and said detector;

a rotating compensator between said source and said sample supporting stage;

a rotating compensator between said sample supporting stage and said detector;

a stokes vector selector between said source and said sample supporting stage;

a stokes vector selector between said sample supporting stage and said detector.

In addition, present invention methodology which involves which the step of providing an ellipsometer or polarimeter system involves the selection of:

a2) a polarization state generator comprising a THz source of electromagnetic radiation that provides substantially polarized output in a frequency range between 300 GHz or lower and extending higher than at least 1 THz; and providing at least one odd bounce optical image rotating system which comprises:

an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector;

is definitely new and Patentable.

This is the case wherein during data collection said odd-bounce optical image rotating system is rotated as a selection from the group consisting of:

step-wise; and
continuously rotated.

Additional basis of Patentability is more particularly provided when the system comprises at least two rotating elements, each thereof being selected from the group consisting of:

rotating polarizer;
rotating compensator;
rotating analyzer; and
said odd-bounce optical image rotating system;

and wherein said selected two rotating elements are both continuously rotated during data acquisition.

It is also presented that an ellipsometer or polarimeter system which operates in the THz range, and its method of use, which ellipsometer or polarimeter comprises a chopper to chop the electromagnetic beam and provide substantially only the chopped electromagnetic beam to the detector, and which is in functional combination with at least two rotating elements, each thereof being selected from the group consisting of:

rotating polarizer;
rotating compensator;
rotating analyzer; and
odd bounce optical image rotating system;

which are caused to rotate during data collection; is believed to be new, novel and non-obvious. This is especially the case where said THz range ellipsometer or polarimeter system comprises at least one continuously rotating odd bounce optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

Continuing, the foregoing was substantially disclosed in Co-Pending Pending application Ser. No. 12/456,791 Filed Jun. 23, 2009. In the following, variations on the foregoing, substantially as disclosed in Provisional Application Ser. No. 61/281,905 Filed Nov. 22, 2009, are discussed.

Much as in the foregoing, a present invention ellipsometer or polarimeter system comprises:

a) a source selected from the group consisting of:
a1) an FTIR source (S2) of electromagnetic radiation in functional combination with a polarization state generator, that provides substantially polarized output in a frequency range above about 1 THz; and
a2) a polarization state generator comprising an FTIR source (S2) of electromagnetic radiation which provides substantially polarized output in a frequency range above about 1 THz.

One difference between that disclosed above, and what is now disclosed, is that the presently disclosed system provides that said polarization state generator is selected from the group consisting of:

a21) a polarization state generator exit polarizer preceded by an odd-bounce polarization state rotation system; and
a22) a polarization state generator exit polarizer preceded by a polarization state generator entry polarizer.

As in the foregoing, a present invention ellipsometer or polarimeter system further comprises:

and a source selected from the group consisting of:
a3) a THz source (S1) of electromagnetic radiation in functional combination with a polarization state generator, that provides substantially polarized output in a frequency range between 300 GHz or lower and extending higher than at least 1 THz.

Another difference between what was disclosed above and what is now disclosed is that the presently disclosed system provides that said polarization state generator is selected from the group consisting of:

a4) a polarization state generator comprising a THz source (S1) of electromagnetic radiation that provides substantially polarized output in a frequency range between 300 GHz or lower and extending higher than at least 1 THz, wherein said polarization state generator is selected from the group consisting of:

a41) a polarization state generator exit polarizer preceded by an odd-bounce polarization state rotation system; and
a42) a polarization state generator exit polarizer preceded by a polarization state generator entry polarizer.

As in the foregoing disclosure, said THz source (S1) of electromagnetic radiation comprising at least one selection from the group consisting of:
a backward wave oscillator (BWO);
a Smith-Purcell cell (SP); and
a free electron laser (FE);
optionally in functional combination with a frequency multiplier (M) for providing harmonics of a fundamental output frequency that provides substantially polarized frequency output in a frequency range between 300 GHz or lower and extending higher than at least 1 THz, and
said ellipsometer or polarimeter system further comprising means for selecting between said THz (S1) and FTIR (S2) sources.

This is followed by:
b) a sample (S) support;
c) a detector system (D1) (D2) (D3) of electromagnetic radiation comprising at least one selection from the group consisting of:
a golay cell (GC) detector; and
a bolometer (BOL) detector.

And said ellipsometer or polarimeter system again further comprises, between said selected source and said selected detector, at least one selection from the group:

a stationary, rotatable or rotating polarizer (P) between said source (S1) (S2) and said sample (S) support;
a stationary, rotatable or rotating analyzer (A) between said sample support (S) and said detector (GC) (BOL); and
a stationary, rotatable or rotating compensator (C) (C') between said source (S) and detector (GC) (BOL).

In use a selected functional combination of selected source, optional polarization state generator, and detector is applied to cause electromagnetic radiation to pass impinge on and interact with a sample on said sample support (S), then enter said selected detector (D1) (D2) (D3), to the end that said detector produces an output.

A specific presently disclosed invention is found where the A2 polarization state generator comprises an FTIR source (S2), and the A4 polarization state generator comprises a THz source (S1), wherein a22 and a42 are further elected.

Another presently disclosed invention is found where the A2 polarization state generator comprises an FTIR source (S2), and the A4 polarization state generator comprises a THz source (S1), wherein a21 and a41 are further elected.

Another presently disclosed invention is found where the A2 polarization state generator comprises an FTIR source (S2), and the A4 polarization state generator comprises a THz source (S1), wherein a21 and a42 are further elected.

Another presently disclosed invention is found where the A2 polarization state generator comprises an FTIR source (S2), and the A4 polarization state generator comprises a THz source (S1), wherein a22 and a41 are further elected.

A method of characterizing a sample comprising the steps of:
A) providing an ellipsometer or polarimeter system as just disclosed;
B) selecting a source and detector and polarization state generator;
C) applying said selected source to cause substantially polarized electromagnetic radiation to impinge on and interact with said sample (S) on said sample support, then proceed to and enter said selected detector, to the end that said detector provides output;
said method further comprising performing at least one selection from the group consisting of:
storing at least some output provided by said detector in machine readable media;
analyzing at least some of the output provided by said detector and storing at least some of the results of said analysis in machine readable media;
displaying at least some output provided by said detector by electronic and/or non-electronic means;
analyzing at least some of the output provided by said detector and displaying at least some of the results of said analysis by electronic and/or non-electronic means;
causing at least some output provided by said detector to produce a signal which is applied to provide a concrete and tangible result;
analyzing at least some of the output provided by said detector and causing at least some thereof to produce a signal which is applied to provide a concrete and tangible result.

Another recitation of a presently disclosed invention is that it is an ellipsometer or polarimeter system comprising:
a) a source of electromagnetic radiation that provides at least partially polarized output in a frequency range between 1.1 THz or lower and extending to 1.4 THZ or higher; and
b) a polarization state generator consisting of a series combination of a exit polarization state generator polarizer preceded by a selection from the group consisting of:
an entry polarization state generator polarizer; and
an odd-bounce polarization state rotation system.

This is followed by:
c) a sample support; and
d) at least one detector of electromagnetic radiation, said at least one detector being capable of detecting electromagnetic radiation in a range of between 300 GHz or lower and extending up at least 1.4 THZ.

Between said source and said detector, there is also present at least one selection from the group:
a stationary, rotatable or rotating polarizer between said THZ source and said sample support;
a stationary, rotatable or rotating analyzer between said sample support and said detector;
a stationary, rotatable or rotating compensator between said source and detector;
in addition to said polarization state generator components.

It is noted that the polarization state generator characterized by a selected odd-bounce polarization state rotation system followed by said polarization state generator exit polarizer operates by the odd-bounce polarization state generator receiving an at least partially polarized beam of electromagnetic radiation from the source thereof, rotating the polarization state of said at least partially polarized beam and passing it through said polarization state exit polarizer which serves to improve the purity of the polarization state exiting therefrom.

It is also noted that the polarization state generator is characterized by a polarization state generator entry polarizer followed by said polarization state generator exit polarizer operates by the polarization state generator entry polarizer receiving an at least partially polarized beam of electromagnetic radiation from the source thereof and then passing it through said polarization state exit polarizer. Said polarization state generator entry polarizer serves to enable avoiding a condition wherein an effective azimuth of the at least partially polarized beam of electromagnetic radiation provided by the source thereof, and that of the polarization state generator exit polarizer present at essentially 90 degrees with respect to one another thereby preventing the at least partially polarized beam of electromagnetic radiation from progressing beyond the polarization state generator exit polarizer.

Another recitation of a present invention ellipsometer or polarimeter system provides that it comprise:
a) a THZ source of electromagnetic radiation that provides at least partially polarized output in a frequency range between 300 GHz or lower and extending to 1.1 THZ or higher; and
b) a polarization state generator consisting of a series combination of a exit polarization state generator polarizer preceded by a selection from the group consisting of:
an entry polarization state generator polarizer; and
an odd-bounce polarization state rotation system.

Said elements are followed by:
c) a sample support; and
d) at least one detector of electromagnetic radiation, said at least one detector being capable of detecting electromagnetic radiation in a range of between 300 GHz or lower and extending up at least 1.1 THZ.

In addition to said polarization state generator components, said ellipsometer or polarimeter system further comprises, between said source and said detector, at least one selection from the group:
a stationary, rotatable or rotating polarizer between said source and said sample support;
a stationary, rotatable or rotating analyzer between said sample support and said detector;

a stationary, rotatable or rotating compensator between said source and detector.

Another recitation of a present invention ellipsometer or polarimeter system provides that it comprise:
- a) an FTIR source of electromagnetic radiation that provides at least partially polarized output in a frequency range between 1.1 THz or lower and extending to 1.4 THZ or higher:
- b) a polarization state generator consisting of a series combination of a exit polarization state generator polarizer preceded by a selection from the group consisting of:
  an entry polarization state generator polarizer; and
  an odd-bounce polarization state rotation system.

Said ellipsometer or polarimeter system then further comprises:
- c) a sample support; and
- d) at least one detector of electromagnetic radiation, said at least one detector being capable of detecting electromagnetic radiation in a range of between 1.1 THz or lower and extending up at least 1.4 THZ.

In addition to said polarization state generator components, said ellipsometer or polarimeter system further comprises, between said source and said detector, at least one selection from the group:
a stationary, rotatable or rotating polarizer between said THZ source and said sample support;
a stationary, rotatable or rotating analyzer between said sample support and said detector;
a stationary, rotatable or rotating compensator between said source and detector.

Continuing, the present invention ellipsometer and polarimeter system can be configured as a Rotating Analyzer, a Rotating Polarizer or a Rotating Compensator system. The preprint paper in the Background Section discloses a Rotating Analyzer system. Reference to FIG. 1p shows that present invention Rotating Analyzer ellipsometer or polarimeter system sequentially comprises:
a backward wave oscillator (BWO);
a focusing lens;
a rotatable image rotation system;
a rotatable wire grid polarizer;
a sample supporting stage;
a rotating analyzer;
a Golay cell;

said ellipsometer or polarimeter system further comprising:
an optical chopper;
between said backward wave oscillator and said Golay cell.
In use a polarized beam of Terahertz spectral range electromagnetic radiation is provided by said backward wave oscillator, is focused by the focusing lens, has its polarization state rotated by said rotatable image rotation system and passes through said rotatable wire grid polarizer, then impinges on a sample placed on said sample supporting stage, reflects therefrom and passes through said rotating analyzer and enters said Golay cell. Said Rotating Analyzer ellipsometer or polarimeter system is distinguished in that, during data acquisition, the rotatable image rotation system and rotatable wire grid polarizer are functionally stepwise rotated in tandem, wherein said rotatable wire grid polarizer is stepwise rotated through a sequence of angles twice that of the rotatable image rotation system, such that the polarization state of the beam provided to the wire grid polarizer by the rotatable image rotation system, is passed by said rotatable wire grid polarizer even where the polarization state of the polarized beam of Terahertz spectral range electromagnetic radiation from the backward wave oscillator is rotated by 90 degrees.

Said Rotating Analyzer ellipsometer or polarimeter system can be characterized by said rotatable image rotation system being an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector, and the at least one odd bounce (OB) (OB') optical image rotating system can consist of a selection from the group consisting of:
three; and
five;
reflective elements.

Said present invention Rotating Analyzer ellipsometer or polarimeter system can further comprise at least one beam directing reflecting means and the sample supporting stage can be part of a 2Ø goniometer.

A variation on the present invention Rotating Analyzer ellipsometer or polarimeter system can sequentially comprise:
a backward wave oscillator (BWO);
optionally a focusing lens;
a rotatable image rotation system;
a rotatable wire grid polarizer;
a sample supporting stage;
a rotating analyzer;
a Golay cell.

Said ellipsometer or polarimeter system further comprises:
an optical chopper;
between said backward wave oscillator and said Golay cell.
In use a polarized beam of Terahertz spectral range electromagnetic radiation is provided by said backward wave oscillator, is optionally focused by the focusing lens, has its polarization state rotated by said rotatable image rotation system and passes through said rotatable wire grid polarizer, then impinges on a sample placed on said sample supporting stage, reflects therefrom and passes through said rotating analyzer and enters said Golay cell.

Said ellipsometer or polarimeter system is distinguished in that, during data acquisition, the rotatable image rotation system and rotatable wire grid polarizer are functionally stepwise rotated in tandem, wherein said rotatable wire grid polarizer is stepwise rotated through a sequence of angles twice that of the rotatable image rotation system, such that the polarization state of the beam provided to the wire grid polarizer by the rotatable image rotation system, is passed by said rotatable wire grid polarizer even where the polarization state of the polarized beam of Terahertz spectral range electromagnetic radiation from the backward wave oscillator is rotated by 90 degrees.

Said ellipsometer or polarimeter system can involve a rotatable image rotation system which is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

Said ellipsometer or polarimeter system at least one odd bounce (OB) (OB') optical image rotating system can consist of a selection from the group consisting of:
  three; and
  five;
reflective elements.

Said ellipsometer or polarimeter system can further comprise at least one beam directing reflecting means.

Said ellipsometer or polarimeter system can involve a sample supporting stage is part of a system for controlling the angle of incidence at which a beam of electromagnetic radiation is caused to approach said sample.

Another recitation of a rotating analyzer ellipsometer or polarimeter system provides that it can sequentially comprise:
  a backward wave oscillator (BWO);
  optionally a focusing lens;
  a rotatable first wire grid polarizer;
  a rotatable second wire grid polarizer;
  a sample supporting stage;
  a rotating analyzer;
  a Golay cell.
Said ellipsometer or polarimeter system further comprises:
  an optical chopper;
between said backward wave oscillator and said Golay cell.

In use a polarized beam of Terahertz spectral range electromagnetic radiation is provided by said backward wave oscillator, is optionally focused by the focusing lens, has its polarization state altered by said first rotatable wire grid polarizer and then by said second rotatable wire grid polarizer, then impinges on a sample placed on said sample supporting stage, reflects therefrom and passes through said rotating analyzer and enters said Golay cell.

Said ellipsometer or polarimeter system is distinguished in that said two rotatable wire grid polarizers are functionally operated in tandem such that the polarization state of the beam provided to the second rotatable wire grid polarizer by the first rotatable wire grid polarizer, is passed by said second rotatable wire grid polarizer, where it not be passed were the first rotatable wire grid polarizer not present and the polarization state of the polarized beam of Terahertz spectral range electromagnetic radiation from the backward wave oscillator is rotated by 90 degrees at the location of said sample.

Said ellipsometer or polarimeter system can further comprise at least one beam directing reflecting means.

Said ellipsometer or polarimeter system can involve a sample supporting stage is part of a system for controlling the angle of incidence at which a beam of electromagnetic radiation is caused to approach said sample.
FA
A fixed analyzer ellipsometer or polarimeter system can sequentially comprise:
  a backward wave oscillator (BWO);
  optionally a focusing lens;
  optionally a rotatable or rotating polarizer;
  a sample supporting stage;
  a rotatable image rotation system;
  a fixed position analyzer;
  a Golay cell.
Said ellipsometer or polarimeter system further comprising:
  an optical chopper;
between said backward wave oscillator and said Golay cell.

In use a polarized beam of Terahertz spectral range electromagnetic radiation is provided by said backward wave oscillator, is optionally focused by the focusing lens, optionally has its polarization state rotated by said rotatable or rotating polarizer, then impinges on a sample placed on said sample supporting stage, reflects therefrom and passes through said rotatable image rotation system and fixed position analyzer and enters said Golay cell.

Said ellipsometer or polarimeter system is distinguished in that, during data acquisition, the rotatable image rotation system is stepwise rotated while the analyzer remains fixed in position.

A present invention Rotating Polarizer ellipsometer or polarimeter system sequentially can comprise:
RP
  a backward wave oscillator (BWO);
  optionally a focusing lens;
  a rotatable or rotating polarizer;
  a sample supporting stage;
  a rotatable image rotation system;
  a rotatable wire grid analyzer;
  a Golay cell.
Said ellipsometer or polarimeter system can further comprise:
  an optical chopper;
between said backward wave oscillator and said Golay cell.

In use a polarized beam of Terahertz spectral range electromagnetic radiation is provided by said backward wave oscillator, is optionally focused by the focusing lens, has its polarization state rotated by said rotatable or rotating polarizer, then impinges on a sample placed on said sample supporting stage, reflects therefrom and passes through said rotatable image rotation system and rotatable wire grid analyzer and enters said Golay cell.

Said ellipsometer or polarimeter system is distinguished in that, during data acquisition, the rotatable image rotation system and rotatable wire grid analyzer are functionally stepwise rotated in tandem, wherein said rotatable wire grid analyzer is stepwise rotated through a sequence of angles twice that of the rotatable image rotation system, such that the polarization state of the beam provided to the rotatable wire grid analyzer by the rotatable image rotation system.

Said ellipsometer or polarimeter system can involve a rotatable image rotation system is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

Said at least one odd bounce (OB) (OB') optical image rotating system can consist of a selection from the group consisting of:
  three; and
  five;
reflective elements.

Said ellipsometer or polarimeter system can further comprise at least one beam directing reflecting means.

Said ellipsometer or polarimeter system can provide that the sample supporting stage is part of a system for controlling the angle of incidence at which a beam of electromagnetic radiation is caused to approach said sample.

A present invention Rotating Compensator ellipsometer or polarimeter system sequentially comprising:
RC
  a backward wave oscillator (BWO);
  optionally a focusing lens;
  a rotatable image rotation system;

a rotatable wire grid polarizer;
a sample supporting stage;
a rotatable analyzer;
a Golay cell.
Said ellipsometer or polarimeter can system further comprise:
an optical chopper; and
a rotating compensator;
between said backward wave oscillator and said Golay cell.

In use a polarized beam of Terahertz spectral range electromagnetic radiation is provided by said backward wave oscillator, is optionally focused by the focusing lens, has its polarization state rotated by said rotatable image rotation system and passes through said rotatable wire grid polarizer, then impinges on a sample placed on said sample supporting stage, reflects therefrom and passes through said rotatable analyzer; said Terahertz spectral range electromagnetic radiation also passing through said optical chopper and rotating compensator; and enters said Golay cell.

Said ellipsometer or polarimeter system is distinguished in that, during data acquisition while said rotating compensator is caused to continuously rotate, the rotatable image rotation system and rotatable wire grid polarizer are functionally stepwise rotated in tandem, wherein said rotatable wire grid polarizer is stepwise rotated through a sequence of angles twice that of the rotatable image rotation system, such that the polarization state of the beam provided to the wire grid polarizer by the rotatable image rotation system, is passed by said rotatable wire grid polarizer even where the polarization state of the polarized beam of Terahertz spectral range electromagnetic radiation from the backward wave oscillator is rotated by 90 degrees Said ellipsometer or polarimeter system can provide that the rotatable analyzer is optionally also stepwise rotated during data acquisition.

Said ellipsometer or polarimeter system can provide that said rotatable image rotation system is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

Said at least one odd bounce (OB) (OB') optical image rotating system consists of a selection from the group consisting of:
three; and
five;
reflective elements.

Said ellipsometer or polarimeter system can further comprise at least one beam directing reflecting means.

Said ellipsometer or polarimeter system can provide that the sample supporting stage is part of a system for controlling the angle of incidence at which a beam of electromagnetic radiation is caused to approach said sample.

Said ellipsometer or polarimeter system can provide that the rotating compensator is present at a selection from the group consisting of:
between the backward wave oscillator and said sample supporting stage; and
said sample supporting stage and said Golay Cell;
and which further comprises a linear polarizer on the same side of the sample stage as is the rotating compensator.

GENERALIZED DISCLOSURE

As further, generalized, disclosure it is presented that a TeraHertz Ellipsometer can be configured from components:

Sources

SOURCE 1=Generalized narrow-band essentially single frequency:
Backward wave oscillator;
Backward wave oscillator with multipliers;
Multiple Backward wave oscillators;
Smith Purcell;
Free Electron;
Mixed-laser-beat+Solid State Emitter
SOURCE 2=Generally Broadband Blackbody dominated:
Globar;
Nerst Glower;
Arc Lamp.
Frequency Purification Systems
THZ FILTER 1+NARROW PASS THZ FILTER
Tunable Diffraction Grating;
Tunable Interferometer;
Dispersive Prism;
THZ FILTER 2+ORDER SORTING
Longpass Absorption Filter;
Shortpass Absorption Filter;
Bandpass Absorption Filter;
THZ FILTER 3
at least one, perhaps more, combination from each of the THZ Filter 1 and THZ Filter 2 categories.

Detectors

DET 1=
Golay Cell;
Cryogenic Bolomete;
Intensity sensitive Solid State Device;
DET 2=
direct Electric Field Sensitive Solid State Device; (for use with mixed laser Source)
DET 3=
Combination of DET 1 and DET 2

Polarization Optical Element for Lock-In Measurements

Changing and element, (stepwise of continuous), provides synchronization to:
Rotating Analyzer (RA);
Rotating Polarizer (RP);
Rotating Compensator (RC);
Stokes Vector Control (ISVC)
(used only with Source 1).
From the above elements two types of THZ Ellipsometer Systems can be configured, namely:
a Scanning Monochromator-like System; and
a Dual System providing Scanning+FTIR System.
Systems which can be Constructed from the Above Elements are:
Scanning Monochromator
REQUIRED SOURCE 1
OPTIONAL THZ FILTER 3
Optional BEAM CHOPPER
(Beam Chopped if more than one RA/RP/RC element continuously rotated during data acquisition)

OPTIONAL Fixed Stokes vector Setting Sub-System (ie. Polarizer or Partial Polarizer);
OPTIONAL Polarizer Rotator between Source and Detector;
REQUIRED RP and/or RA and/or RC and/or 2nd RC and/or ISVC and/or 2nd ISVC;
REQUIRED Sample Stage with Reflection and/or Transmission capability;
OPTIONAL Variable Angle capability;
OPTIONAL 2nd Polarization Rotator between Source and Detector;
OPTIONAL Fixed Stokes Vector Detecting Sub System (ie. Polarizer or Partial Polarizer);
OPTIONAL THZ Filter 3;
REQUIRED Detector 1.
Dual System: Scanning+Ftir System
REQUIRED Source 1+
OPTIONAL THZ Filter 3; and
REQUIRED Source 2 and FTIR Modulating System; and
OPTIONAL Chopper (Beam Chopped if more than one RA/RP/RC element continuously rotated during data acquisition);
OPTIONAL Fixed Stokes Vector Setting Sub-System (ie. Polarizer or Partial Polarizer); (eg. in common or separate for Source 1 and Source 2 beam paths);
OPTIONAL Polarization Rotator between Source and Detector; (eg. in common or separate for Source 1 and Source 2 beam paths);
OPTIONAL ISVC; (used only with RP and/or RA and/or RC and/or second RC; (eg. in common or separate for Source 1 and Source 2 beam paths);
Required Sample Stage; (with Reflection and/or Transmission capability;
OPTIONAL Variable Angle capability, common or nearly common measurement spot on Sample, but not necessarily at same Angle of Incidence);
OPTIONAL 2nd Pol Rotator between Source and Detector; (eg. in common or separate for Source 1 and Source 2 beam paths);
OPTIONAL Fixed Stokes Vector Detecting Sub System (ie. Polarizer or Partial Polarizer); (eg. In common or separate for Source 1 and Source 2 beam paths);
OPTIONAL THZ Filter 3; (eg. in common or separate for Source 1 and Source 2 beam paths);
REQUIRED Detector 3 for use with Source 1; and
REQUIRED Detector 1 for use with Source 2; (eg. in common or separate for Source 1 and Source 2 beam paths).

The foregoing outline provides basis for describing specific present invention systems.

First, a scanning monochromater system for application in the Terahertz frequency range, can comprise:
a narrow-band essentially single frequency source selected from the group consisting of:
   a Backward wave oscillator;
   a Backward wave oscillator with multipliers;
   a Multiple Backward wave oscillators;
   a Smith Purcell;
   a Free Electron;
   a Mixed-laser-beat+Solid State Emitter;
and a detector selected from the group consisting of:
   Golay Cell;
   Cryogenic Bolometer;
   Intensity sensitive Solid State Device;
between said narrow-band essentially single frequency source and said detector, there being a sample supporting stage with reflection and/or transmission capability;
said scanning monochromater system further comprising, between said narrow-band essentially single frequency source and said detector at least one component which is caused to rotate during use, and which is selected from the group consisting of:
   a rotating polarizer between said source and said sample supporting stage;
   a rotating analyzer between said sample supporting stage and said detector;
   a rotating compensator between said source and said sample supporting stage;
   a rotating compensator between said sample supporting stage and said detector;
   a stokes vector selector between said source and said sample supporting stage;
   a stokes vector selector between said sample supporting stage and said detector;
such that in use a sample is placed on said sample supporting stage and a beam of electromagnetic radiation provided by said selected source is caused to interact with said sample, then enter said selected detector.

Said scanning monochromater system can further comprise at least one selection from the group:
   a fixed stokes vector setting polarizer or partial polarizer between said narrow-band essentially single frequency source and said sample supporting stage;
   a fixed stokes vector setting polarizer or partial polarizer between said sample supporting stage and said selected detector.

Said scanning monochromater system can further comprise at least one polarization state rotating system between said selected source and selected detector.

Said scanning monochromater system can comprise two polarization state rotating systems between said selected source and selected detector.

Said scanning monochromater system can further comprise a beam chopper, said beam chopper being applied to chop said beam of electromagnetic radiation during use.

Said scanning monochromater system can, during use, cause said electromagnetic beam to be chopped by said beam chopper while two elements selected from the group consisting of:
   a rotating, polarizer between said source and said sample supporting stage;
   a rotating analyzer between said sample supporting stage and said detector;
   a rotating compensator between said source and said sample supporting stage;
   a rotating compensator between said sample supporting stage and said detector;
   a stokes vector selector between said source and said sample supporting stage;
   a stokes vector selector between said sample supporting stage and said detector;
are caused to rotate.

Said scanning monochromater system can further comprise means for controlling the angle of incidence at which said beam of electromagnetic radiation from said selected source approaches said sample.

Said scanning monochromater system can further comprise, between said selected source and selected detector, at least one terahertz filter and narrow pass THZ filter selected from the group:

Tunable Diffraction Grating;
Tunable Interferometer;
Dispersive Prism;
and/or
at least one THZ filter and order sorting filter selected from the group consisting of:
  Longpass Absorption Filter;
  Shortpass Absorption Filter;
  Bandpass Absorption Filter.
Said scanning monochromater system can further comprise a rotatable polarizer, the rotation of which is synchronized to that of the said at least one polarization state rotating system between said selected source and selected detector.

Said scanning monochromater system can further comprise a lock-in system referenced to said at least one component selected from the group of said:
  rotating polarizer between said source and said sample supporting stage;
  rotating analyzer between said sample supporting stage and said detector;
  rotating compensator between said source and said sample supporting stage;
  rotating compensator between said sample supporting stage and said detector;
  stokes vector selector between said source and said sample supporting stage;
  stokes vector selector between said sample supporting stage and said detector;
for synchronizing the operation thereof to said at least one detector selected from the group consisting of said:
  Golay Cell;
  Cryogenic Bolometer;
  Intensity sensitive Solid State Device;

Another present invention system is a dual scanning and FTIR system for application in the Terahertz and Infrared frequency range, comprising:
  a source for providing Thz range electromagnetic radiation selected from the group consisting of:
    a backward wave oscillator;
    a backward wave oscillator with multipliers;
    multiple Backward wave oscillators;
    a Smith Purcell;
    a free electron; and
    a mixed-laser-beat+solid state emitter;
said dual scanning and FTIR system further comprising a source for providing generally broadband blackbody range electromagnetic radiation selected from the group consisting of:
  a Globar source;
  a Nerst Glower source;
  an arc lamp source;
in functional combination with a FTIR modulating system;
said dual scanning and FTIR system further comprising at least one detector selected from the group consisting of
  a Golay Cell;
  a cryogenic bolometer;
  an intensity sensitive solid state device;
  a direct electric field sensitive solid state device;
said dual scanning and FTIR system further comprising at least one selection from the group consisting of:
  a rotating analyzer;
  a rotating polarizer; and
  at least one rotating compensator;
and a sample supporting stage with reflection and/or transmission capability between said selected sources and said selected detector.

Said dual scanning and FTIR system for application in the Terahertz and Infrared frequency range can further comprise, in combination with the selected source for providing Thz range electromagnetic radiation which is selected from the group consisting of:
  a backward wave oscillator;
  a backward wave oscillator with multipliers;
  multiple Backward wave oscillators;
  a Smith Purcell;
  a free electron; and
  a mixed-laser-beat+solid state emitter;
at least one selection from the group consisting of:
  a tunable diffraction grating;
  a tunable interferometer;
  a dispersive prism;
  and/or
at least one selection from the group consisting of:
  a longpass Absorption Filter;
  a shortpass Absorption Filter;
  a bandpass Absorption Filter.

Said dual scanning and FTIR system for application in the Terahertz and Infrared frequency range can further comprise a fixed stokes vector setting sub-system polarizer or partial polarizer positioned in the path of at least one electromagnetic beam from a selection from the group consisting of:
  said selected source for providing Thz range electromagnetic radiation; and
  said FTIR source.

Said dual scanning and FTIR system can further comprise a second fixed stokes vector setting sub-system polarizer or partial polarizer positioned in the path of at least one electromagnetic beam from a selection from the group consisting of:
  said selected source for providing Thz range electromagnetic radiation; and
  said FTIR source.

Said dual scanning and FTIR system for application in the Terahertz and Infrared frequency range can further comprise at least two rotating elements, selected from the group:
  rotating polarizer and rotating analyzer;
  rotating polarizer and rotating compensator;
  rotating analyzer and rotating compensator;
  two rotating compensators;
Said dual scanning and FTIR system for application in the Terahertz and Infrared frequency range can further comprise an ISVC fixed stokes vector control selecting sub-system polarizer or partial polarizer positioned in the path of at least one electromagnetic beam from a selection from the group consisting of:
  said selected source for providing Thz range electromagnetic radiation; and
  said FTIR source.

Said dual scanning and FTIR system for application in the Terahertz and Infrared frequency range can further comprise at least one polarization state rotating system between said selected source and selected detector positioned in the path of at least one electromagnetic beam from a selection from the group consisting of:
  said selected source for providing Thz range electromagnetic radiation; and
  said FTIR source.

Said dual scanning and FTIR system for application in the Terahertz and Infrared frequency range can further comprise a second polarization state rotating system between said selected source and selected detector positioned in the path of at least one electromagnetic beam from a selection from the group consisting of:

said selected source for providing Thz range electromagnetic radiation; and
said FTIR source.

Said dual scanning and FTIR system can, during use, provide that said electromagnetic beam is caused to be chopped by a beam chopper while two elements selected from the group consisting of:
- a rotating polarizer between said source and said sample supporting stage;
- a rotating analyzer between said sample supporting stage and said detector;
- a rotating compensator between said source and said sample supporting stage;
- a rotating compensator between said sample supporting stage and said detector;
- a stokes vector selector between said source and said sample supporting stage;
- a stokes vector selector between said sample supporting stage and said detector;

are present and are caused to rotate.

Said dual scanning and FTIR system can further comprise means for controlling the angle of incidence at which said beam of electromagnetic radiation from said selected source approaches said sample.

Said scanning monochromater system can further comprise a rotatable polarizer, the rotation of which is synchronized to that of the said at least one polarization state rotating system between said selected source and selected detector.

Said dual scanning and FTIR system can further comprise a lock-in system referenced to said at least one component selected from the group:
- rotating polarizer between said source and said sample supporting stage;
- rotating analyzer between said sample supporting stage and said detector;
- rotating compensator between said source and said sample supporting stage;
- rotating compensator between said sample supporting stage and said detector;
- stokes vector selector between said source and said sample supporting stage;
- stokes vector selector between said sample supporting stage and said detector;

for synchronizing the operation thereof to said at least one detector selected from the group consisting of said:
- a Golay Cell;
- a cryogenic bolometer;
- an intensity sensitive solid state device;
- a direct electric field sensitive solid state device.

The present invention will be better understood by reference to the Detailed Description Section of this Specification, in combination with the Drawings.

BRIEF DESCRIPTION OF THE DRAWINGS

FIGS. 1l-1o demonstrate various element configurations for a Terahertz ellipsometer or polarimeter.

FIG. 1p shows specific Terahertz ellipsometer or polarimeter.

DETAILED DESCRIPTION

Figure 1A:
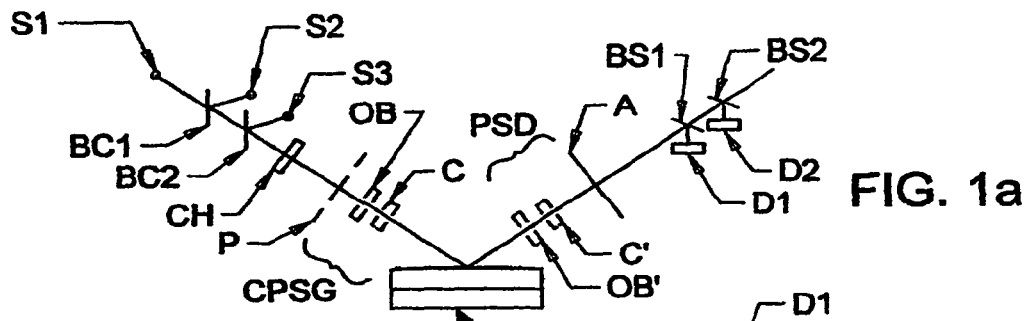
FIGS. 1a-1c show demonstrative configurations for a present invention ellipsometer or polarimeter system.
Figure 1B:
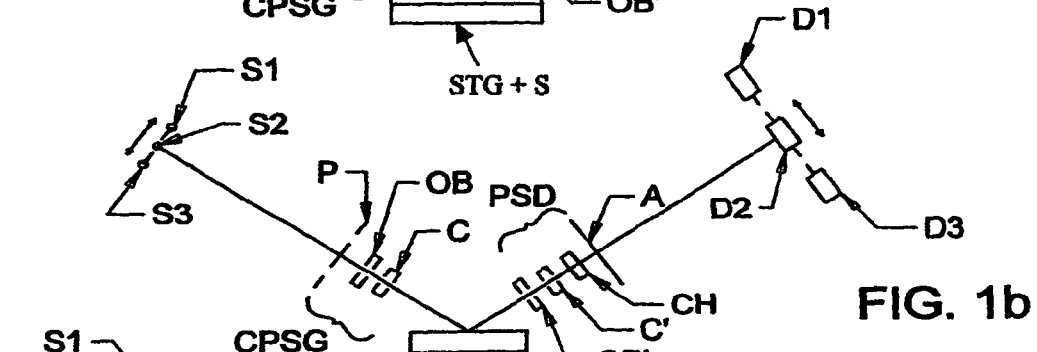
Figure 1C:
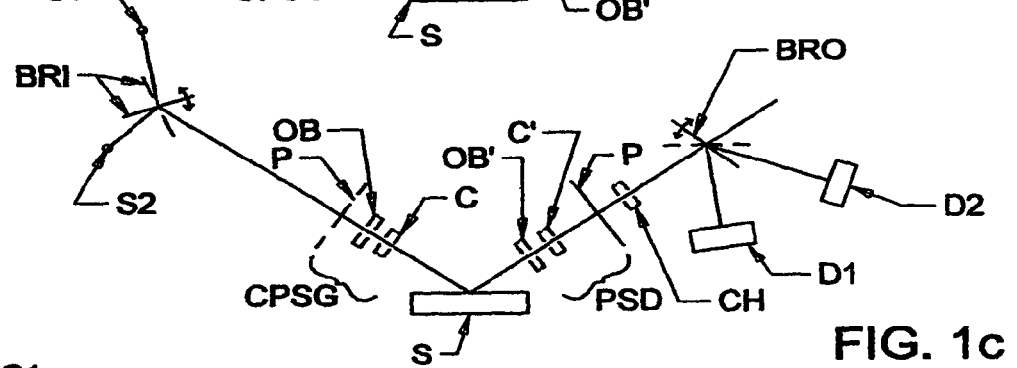

Turning now to the Drawings, FIGS. 1a, 1b and 1c show various approaches to providing a Present Invention System. FIG. 1a shows Three Sources (S1) (S2) S3), which can each be a backward wave oscillator or a Smith-Purcell cell or a free electron laser or a solid state device. Also demonstrated are Beam Combiners (BC1) (BC2) (BC3) which serve to direct electromagnetic radiation from Sources (S1) (S2) S3), respectively, toward a Sample (S), via optional Polarizer (P), (the natural source polarization can suffice), Odd Bounce Image Rotating System (OB) and Compensator (C). Said optional (P) (OB) (C) components are shown as typically, in combination, being termed a Conventional Polarization State Generator (CPSG) and are included to polarize a beam of electromagnetic radiation provided by a Source (S1) (S2) S3). As regards the Present Invention, however, it is possible that a selected Source (S1) (S2) S3) can provide a beam of electromagnetic radiation which is already polarized, therefore, in this Specification it is to be understood that it is within the definition of "Polarization State Generator (PSG)" that it comprise the Source (S1) (S2) S3) with or without the presence of Conventional Polarization State Generator (CPSG) components. FIG. 1a also shows that optional (OB') (C') and (P) components between the Sample (S) and a Detector (D1) D2). Note that Detectors (D1) and (D2) have electromagnetic radiation directed thereinto by Beam Splitters/Directors. In use Source (S1) (S2) and (S3) can be energized or not so that a beam of electromagnetic radiation progressing toward the Sample (S) comprises various ranges of wavelengths. For instance, Source (S1) can be selected to provide Terahertz (Thz) frequencies, and Source (S2) selected to provide Infrared (IR) frequencies, and during use one or the other can be energized so that only (THz) or (IR) wavelengths are provided, or both can be energized to provide a broad combined range of wavelengths, preferable with an overlap range of between about 1.0 Thz, and 1.4 Thz or higher, frequency. The same general description of FIG. 1a applies to FIGS. 1b and 1c, with the exception that the Sources and Detectors are shown as configured differently. In FIG. 1b the Sources (S1) (S2) (S3) and Detectors (D1) (D2) (D3) are simply sequentially slid into position. In FIG. 1c, Input Beam Reflecting Means (BRI) and Output Beam Reflecting Means (BRO) are shown as being rotatable to selectively direct electromagnetic radiation from one source or another toward the Sample (S). The configurations shown in FIGS. 1a-1c are not to be considered limiting, but rather are demonstrative. For instance, it is possible to choose a FIG. 1a Source selection approach, and a FIG. 1b or 1c Detector selection arrangement etc. And it is within the scope of the Present Invention to provide only one Source, (ie. a Terahertz frequency providing system), while providing a selection between two Detectors (eg. a Golay cell or Bolometer).

It is also noted that the configuration in FIG. 1a can be operated with a plurality of Sources simultaneously turned on to provide an electromagnetic beam which contains a broad frequency range. Especially, but not exclusively, in such a configuration it is beneficial to adjust said sources providing output in the range of 1.0 to 1.4 THz such that substantially the same results, (eg. ellipsometric PSI and/or DELTA), are achieved by analyzing output from any of the selected detectors in the frequency range of between about 1.0 to 1.4 THz. This not only provides continuity between the lower and upper extents of the frequency range, but provides an approach to assuring accuracy of results. If the same results are achieved using very different sources of electromagnetic radiation, both can be considered to very likely enabling acquisition of good data.

Figure 1D:
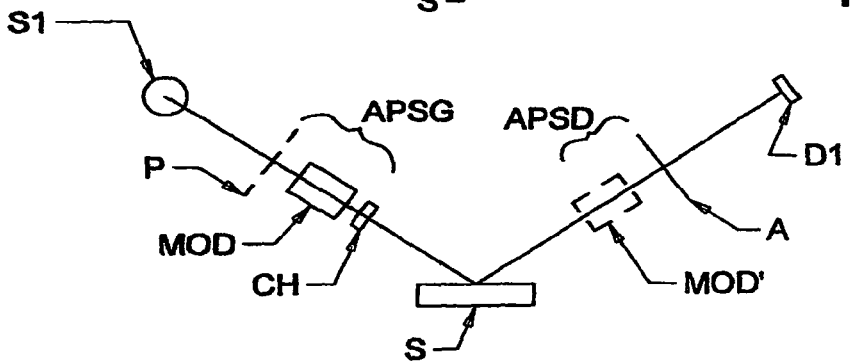
FIG. 1d shows an alternative polarization state generator involving a modulator.

FIG. 1d is included to disclose that an Alternative Polarization State Generator (APSG) configuration involving an optional Polarizer (P) and a Modulator (MOD), can be applied in the present invention. Such an (APSG) configuration can be employed instead of, or in addition to components in the Conventional Polarization State Generator (CPSG) shown in FIGS. 1a-1c. Also indicated is an Alternative Polarization State Detector Generator (APSD) configuration including a Modulator (MOD'). Again such an (APSD) configuration can be employed instead of, or in addition to the Conventional Polarization State Detector (CPSD) shown in FIGS. 1a-1c. It is noted that various types of Modulators exist, including those which apply an electric signal, or an acoustic signal or an optical signal to effect modulation of a polarization state.

Also shown in FIGS. 1a-1d is a Chopper (CH). This allows the beam to be "chopped" at a selected frequency so that it can be monitored separate from non-chopped background electromagnetic radiation. This enables obtaining data which is not overwhelmed by noise, in a non-darkened room. The Chopper (CH) is shown a being located differently in each of FIGS. 1a-1d. This is to indicate that there is no required position, with the only functional requirement being that the beam be chopped thereby. The system which comprises a Chopper (CH) will provide substantially only the chopped electromagnetic beam to the Detector (D1) (D2) D3).

Figure 1E:
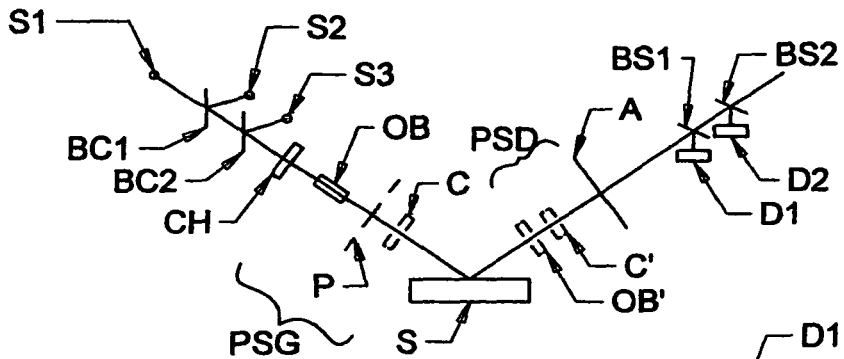
FIGS. 1e-1g show systems similar to those in FIGS. 1a-1c, with the relative positions of the Odd Bounce image rotation system and Polarizer reversed.

FIG. 1e shows a system substantially similar to that in FIG. 1a, but note that the Odd Bounce Image Rotating System (OB) precedes the Polarizer (P) in the Polarization State Generator (PSG). FIG. 1h also indicates that both the Odd Bounce Image Rotating System (OB) and Polarizer (P) are fitted with means, (eg. steppe motors), for effecting synchronized rotation of (MOB) and (MOP). In use a natural polarization state from the Source (S1) is azimuthally rotated by the Odd Bounce Image Rotating System (OB) and then passes through the Polarizer (P). In this system the Polarizer (P) is rotated azimuthally to correspond to the azimuthal position of the polarization in the electromagnetic beam as it exits the Odd Bounce Image Rotating System (OB). This approach has been found to work very well. The Odd Bounce Image Rotating System (OB) is substantially responsible for setting the azimuthal orientation of the beam polarization, and the Polarizer (P) "cleans-up" polarization of the beam exiting. therefrom. FIGS. 1f and 1g are again very similar to FIGS. 1b and 1c, but with a similar reversal of position of the Odd Bounce Image Rotating System (OB) and the Polarizer, for the same purpose as indicated with respect to FIGS. 1e and 1a.

Figure 1F:
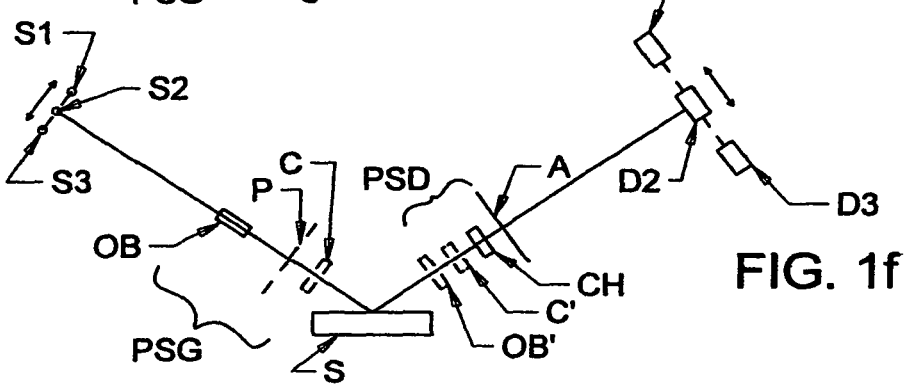
Figure 1G:
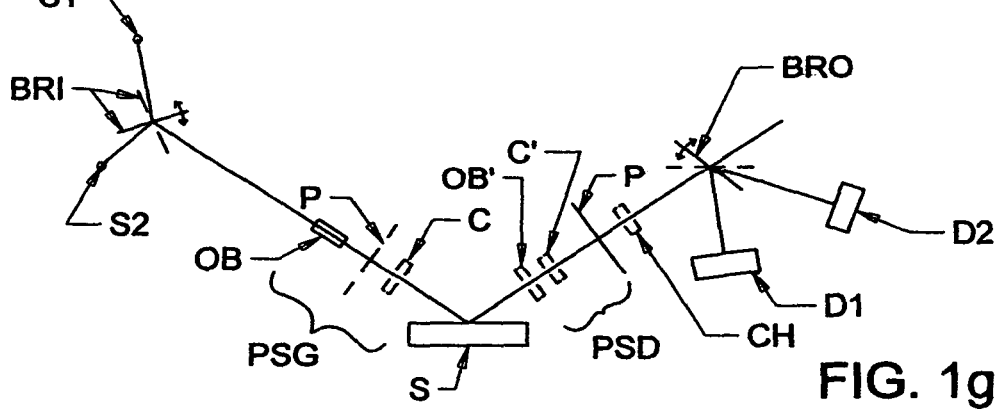
Figure 1H:
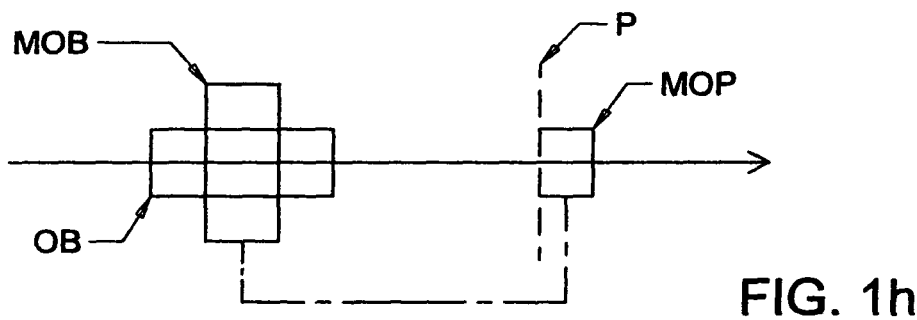
FIG. 1h indicate that the Odd Bounce image rotation system Polarizer reversed are controlled in synchrony.
Figure 1I:
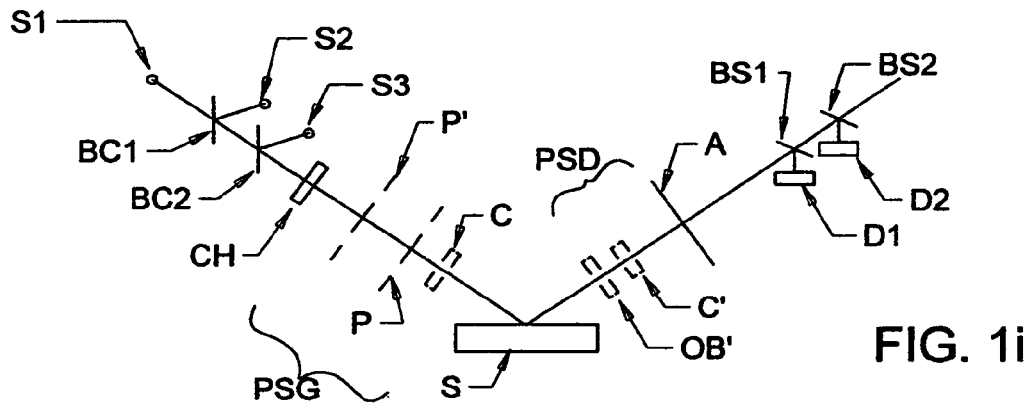
FIGS. 1i-1k are similar to FIGS. 1e-1g, but with the Odd Bounce image rotation system replaced with a second Polarizer.
Figure 1J:
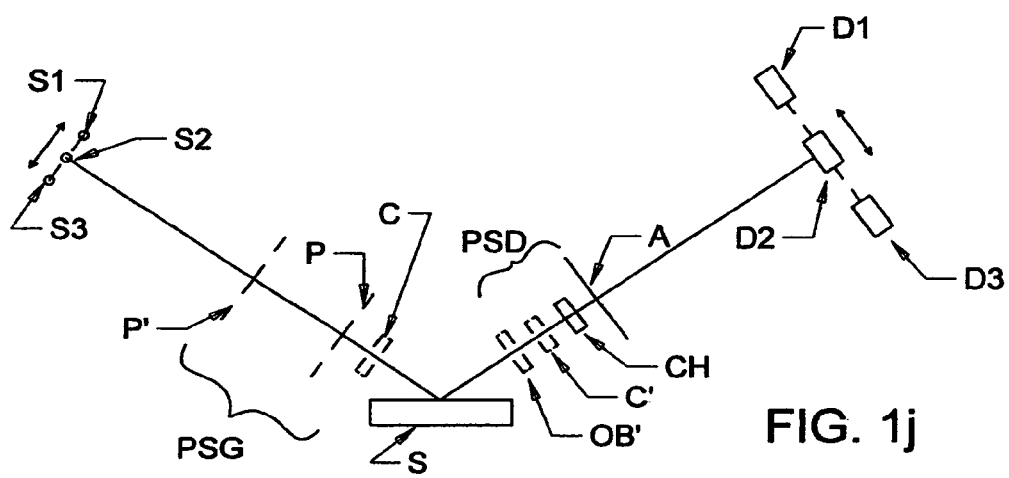
Figure 1K:
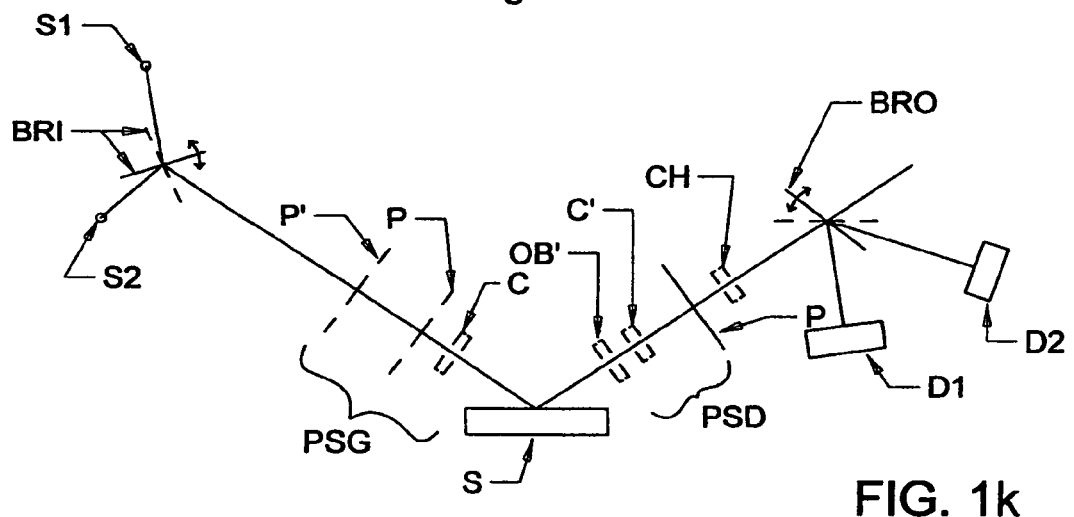

FIGS. 1i-1k show similar configurations to FIGS. 1e-1g, but note that a second Polarizer (P') replaces the Odd Bounce Image Rotating Systems (OB) in FIGS. 1e-1g. In this case the second Polarizer (P') serves to prevent Polarizer (P) being oriented so that it is at 90 degrees with respect to the natural polarization emerging from the Source (1) (S2) (S3), therefore blocking its transmission therethrough. By adding Polarizer (P') it is possible to set Polarizer (P) at any azimuthal orientation and still achieve electromagnetic beam transmission therethrough.

FIGS. 1l-1o demonstrate various element configurations for a Terahertz ellipsometer or polarimeter.

FIGS. 1l and 1p show a Backward Wave Oscillator (BWO) is shown as Source for providing a partially linearly polarized Beam of electromagnetic radiation which is directed to pass through a focusing Lens (L), a Chopper (C), an Image Rotator (PR), a Polarizer (P) then interact with a Sample on a Stage (S), and then pass through a Rotating Analyzer (A) and enter a Golay Cell Detector (GC). More specifically FIG. 11p demonstrates an ellipsometer or polarimeter system sequentially comprising:

a backward wave oscillator (BWO); optionally a focusing lens (L);
a rotatable image rotation system (PR);
a rotatable wire grid polarizer (P);
a sample supporting stage (S);
a rotating analyzer (A);
a Golay cell (GC);

said ellipsometer or polarimeter system further comprising:
an optical chopper (CH);
between said backward wave oscillator (BWO) and said Golay cell (GC);
such that in use a polarized beam of Terahertz spectral range electromagnetic radiation is provided by said backward wave oscillator (BWO), is optionally focused by the focusing lens (L), has its polarization state rotated by said rotatable image rotation system (PR) and passes through said rotatable wire grid polarizer (P), then impinges on a sample placed on said sample supporting stage (S), reflects therefrom and passes through said rotating analyzer and enters said Golay cell;
said ellipsometer or polarimeter system being distinguished in that, during data acquisition, the rotatable image rotation system (PR) and rotatable wire grid polarizer (P) are functionally stepwise rotated in tandem, wherein said rotatable wire grid polarizer (P) is stepwise rotated through a sequence of angles twice that of the rotatable image rotation system (PR), such that the polarization state of the beam provided to the wire grid polarizer (P) by the rotatable image rotation system PR), is passed by said rotatable wire grid polarizer (P) even where the polarization state of the polarized beam of Terahertz spectral range electromagnetic radiation from the backward wave oscillator (BWO) is rotated by 90 degrees.

Said ellipsometer or polarimeter system can provide that said rotatable image rotation system (PR) is an odd bounce (OB) (OB') optical image rotating system comprising an odd number of at least three (RE1) (RE2) (RW3) reflective elements, (see FIGS. 3a and 3b), oriented such that a beam of electromagnetic radiation provided by said source of electromagnetic radiation (BWO) interacts with each of said at least three reflective (RE1) (RE2) (RW3) elements of said at least one odd bounce optical image rotating system (PR) and exits therefrom along a non-deviated non-displaced trajectory, said beam of electromagnetic radiation also interacting with a sample system placed on said stage for supporting a sample system (S), and said analyzer (A) before entering said detector (CC). It is noted that the at least one odd bounce (OB) (OB') optical image rotating system consists of a selection from the group consisting of:

three (RE1) (RE2) (RW3); and
five (RE1') (RE2') (RW3') (RE4') (RE5');
reflective elements.

FIG. 1p shows that said ellipsometer or polarimeter system which can further comprises at least one beam directing reflecting means (M1) (M2) (M3) (M4). Further, the sample supporting stage (S) can be part of a system (HG) for controlling the angle of incidence (Oa) at which a beam of electromagnetic radiation is caused to approach said sample.

Reference to FIGS. 1a-1o should be understood to show that the FIG. 1p system can comprise at least one rotatable or rotating polarizer, compensator and/or analyzer.

FIG. 1m is not to be confused with that in FIGS. 1l and 1p. Ithows a variation of the Rotating Analyzer THZ Ellipsometer system wherein the Image Rotating System is replaced with a second Polarizer (P2). In use relative rotation of Polarizers (P1) and (P2) adjusts the amount of polarized beam which exits (P2).

FIG. 1n shows a Rotating Polarizer THZ Ellipsometer system. Note that compared to FIG. 1l, FIG. 1n shows a Rotating Polarizer (RP) and a combination of Rotatable Analyzer (A) and Image Rotator (PR) after the Sample and Stage (S). The order of the Rotatable Analyzer (A) and Image Rotator (PR) can be reversed.

FIG. 1o shows a Rotating Compensator THZ Ellipsometer system. Note that both the Polarizer (P) and Analyzer (A) are rotatable, and an additional Rotating Compensator (RC) element is present.

Figure 2A:
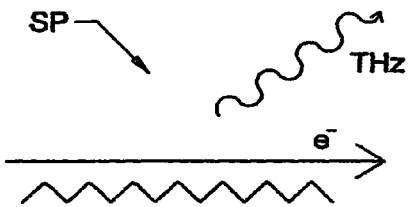
FIGS. 2a-2d show various aspects of Terahertz frequency Sources.
Figure 2B:
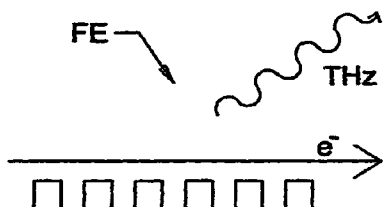
Figure 2C:
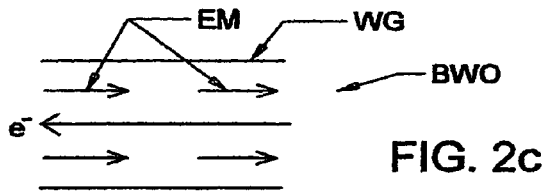
Figure 2D:
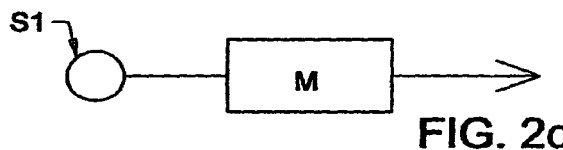

Turning now to FIGS. 2a-2d, insight to the operation of various Terahertz sources is provided. FIG. 2a shows that a Smith-Purcell (SP) cell comprises a Grating (G) and an electron beam (e⁻) passing thereover, with the result being that THz electromagnetic radiation is emitted. FIG. 2b shows that a Free Electron Laser (FE) comprises a sequence of Magnetic Poles (MP), and again an electron beam (e⁻) passing thereover, with the result being that THz electromagnetic radiation is emitted. FIG. 2c shows a Backward Wave Oscillator (BWO) comprises a Waveguide (WG) through which electromagnetic radiation (EM) is passed in one direction while an electron beam (e⁻) passes therethrough in the opposite direction, again with the result that THz electromagnetic radiation is emitted. FIG. 2d demonstrates that a Terahertz source, (arbitrarily identified as (S1)), typically requires that a Frequency Multiplier (M) be present to provide an extended frequency range output, (eg. from 300 GHz or below through at lest 1.4 THz). While not diagrammatically shown, as there is really nothing to show, it is noted that an IR range Source of electromagnetic radiation is preferably a Fourier Transform Infrared (FTIR) Source which provides a spectroscopic range of wavelengths. It is noted that (FTIR) actually refers to an approach in analysis of a spectrum of wavelengths involving use of a means for collecting a multiplicity of wavelengths simultaneously, and application of a Fourier Transform to data, rather than via use of a monochromator. However, it is common to identify the Source of the spectrum of IR wavelengths as an FTIR Source. It is specifically noted that while the Odd-Bounce Image Rotation System, (see FIGS. 3a and 3b), is present in the IR-VASE®, it has never been applied at frequencies below 10 THz. And specifically, it has not been applied in systems comprising a Backward Wave Oscillator (BWO) or a Smith-Purcell cell or a Free Electron Laser which provide frequencies down to 300 GHz or below; The application thereof at said frequencies is new with the present invention. It is also new with the present invention to combine a FTIR Source with a Backward Wave Oscillator (BWO) or a Smith-Purcell cell or a Free Electron Laser to provide a practical system for practicing ellipsometry over a wide frequency range of from 300 GHz or below upward through the IR range.

Figure 2E:
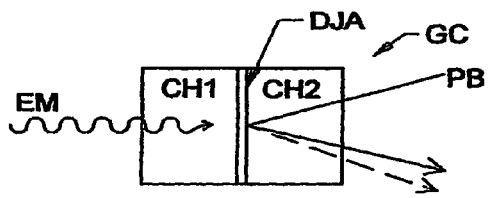
FIGS. 2e-2g show a demonstrative detectors of Terahertz frequencies.
Figure 2F:
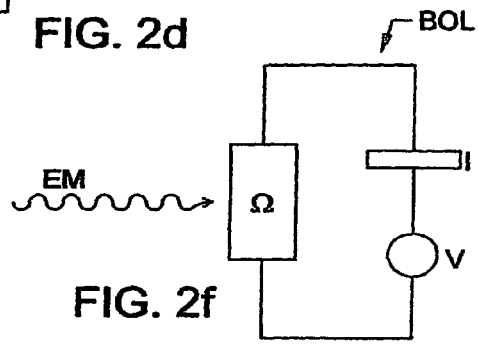
Figure 2G:
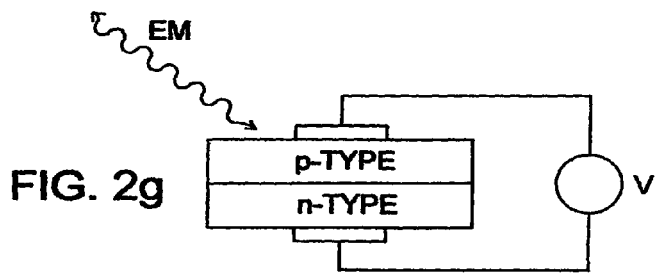

FIGS. 2e and 2f demonstrate basic components of Detectors, (eg. Golay cell (GC) and Bolometer (BOL)). A Golay cell basically comprises two Chambers (CH1) and (CH2). In use electromagnetic radiation (EM) enters one Chamber (CH1) and heats a gas therein, which expands. This causes the Diaphragm (DIA) to change shape which causes a Probe Beam (PB) entered to the Second Chamber (CH2) to reflect along a different pathway which is then detected by a detector (not shown). FIG. 2f shows that a Bolometer (BOL) operates by directing a electromagnetic radiation to impinge on a material ($\Omega$) which changes resistance with its temperature. Also shown are a Voltage Source (V) and a Current Detector (I). In use a change in the current flow indicates that the electromagnetic radiation has heated the material ($\Omega$). FIG. 2g show a demonstrative detector of Terahertz frequencies comprises a P/N junction onto which electromagnetic radiation (EM) is impinged, and which produces a measurable voltage (V). Further, while many materials can be applied in solid state devices, a particularly relevant material for application in THz and IR frequency ranges is disclosed as being "Deuterated Triglycine Sulfate", which is typically referred to as (DTGS), optionally embedded in Poly-Vinylidene Fluoride (PVDF). Said material shows very high pyroelectric performance.

(Note, FIG. 2g should also be considered to present at least a portion of a solid state Source of Terahertz frequencies, wherein a voltage is applied, and electromagnetic radiation emission results. It is to be understood that Solid State Sources and Detectors for providing and detecting THz and/or IR frequency range electromagnetic radiation can be substituted for, or used in combination with any of the other types of Source and Detector types identified herein).

Figure 3A:
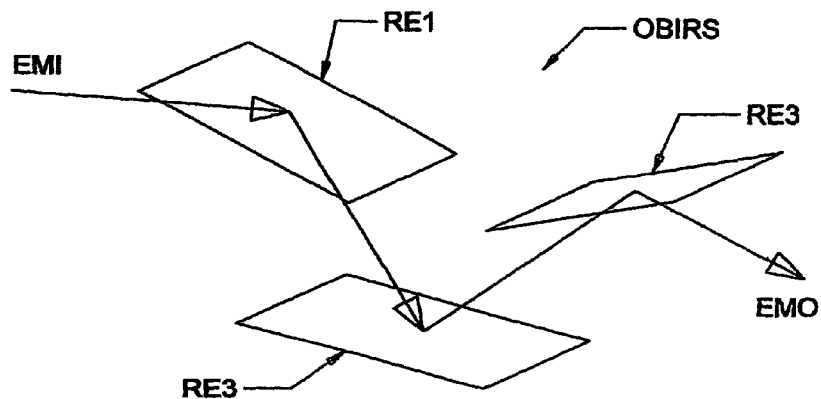
FIG. 3a demonstrates an Odd Bounce image rotating system comprising three (3) reflecting elements.
Figure 3B:
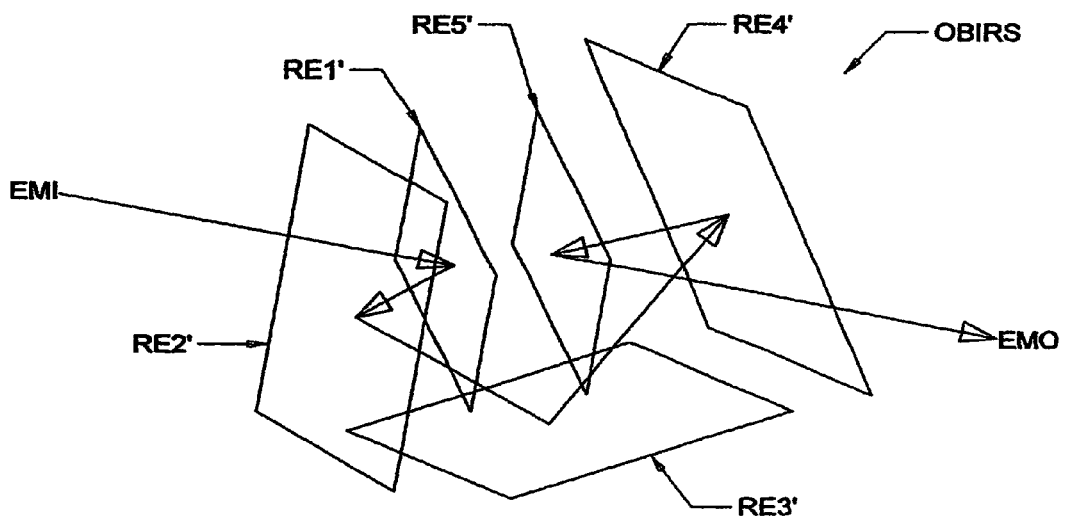
FIG. 3b demonstrates an Odd Bounce image rotating system comprising five (5) reflecting elements.

Turning now to FIGS. 3a and 3b, there is represented in FIG. 3a a three (3) bounce Odd Bounce image rotating system (OBIRS) comprising three (3) reflective elements (RE1), (RE2) and (RE3), oriented with respect to one another such that an input beam of electromagnetic radiation (EMI) exits as an output beam of electromagnetic radiation (EMO) without any deviation or displacement being entered into the locus thereof. FIG. 3b demonstrates a five (5) bounce odd bounce image rotating system (OBIRS) wherein five reflective elements (RE1'), (RE2') (RE3'), (RE4') and (RE5') oriented with respect to one another such an input beam of electromagnetic radiation (EMI) exits as an output beam of electromagnetic radiation (EMO) without any deviation or displacement being entered into the locus thereof. Note generally that the angle of incidence of the (EMI) and (EMO) beams of electromagnetic radiation are nearer normal than is the case in the FIG. 3a three (3) bounce odd bounce image rotating system (OBIRS). This is beneficial in that the closer to normal the angle of incidence, the less aberration effects are entered to the beam. However, it is also to be appreciated that construction of the FIG. 3b system is more difficult than is construction of a FIG. 3a system.

Figure 4:
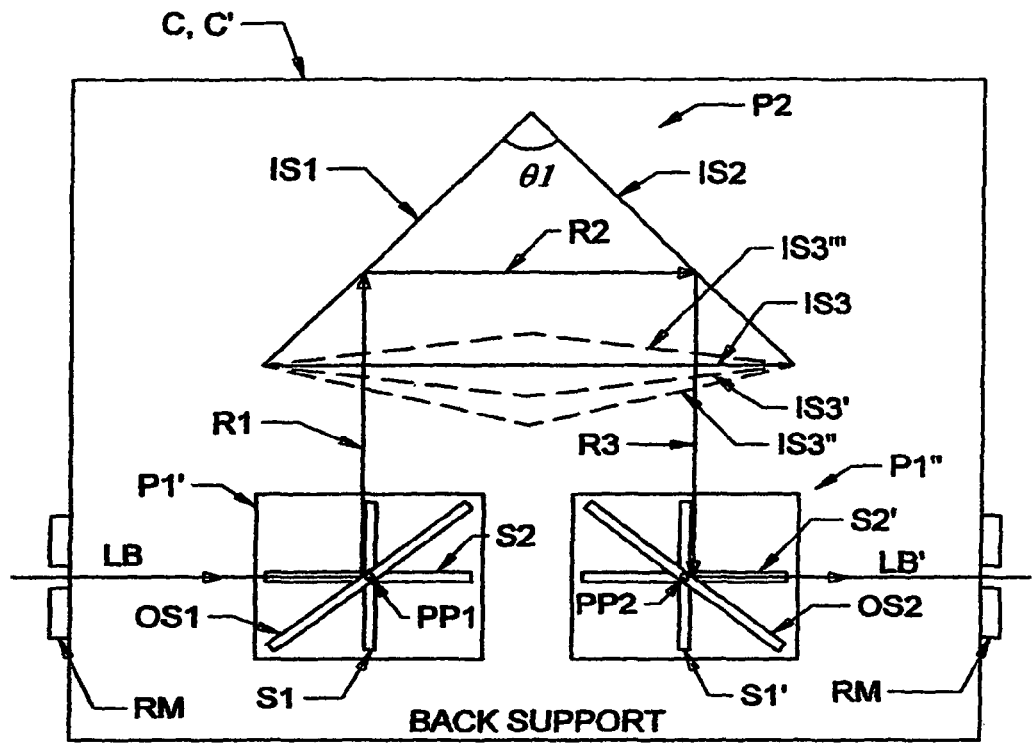
FIG. 4 demonstrates a preferred compensator (C) (C') C") which has been used in a rotating compensator ellipsometer system for application in the IR range of wavelengths.

FIG. 4 demonstrates a preferred compensator (C) (C') for use in a rotating compensator ellipsometer system for application in the IR range of wavelengths. The compensator system comprises, as shown in upright side elevation, first (OS1) and second (OS2) orientation adjustable mirrored elements which each have reflective surfaces. Note the adjustability enabling pivot (PP1) (PP2) mountings. Said compensator system further comprises a third element (TE) which, as viewed in upright side elevation presents with first (IS1) and second (IS2) sides which project to the left and right and downward from an upper point (UP2), said third element (TE) being made of material which provides reflective interfaces on first and second sides inside thereof. Said third element (TE) is oriented with respect to the first (OS1) and second (OS2) orientation adjustable elements such that in use an input electromagnetic beam of radiation (LB) caused to approach one of said first (OS1) and second (OS2) orientation adjustable mirrored elements along an essentially horizontally oriented locus, is caused to externally reflect therefrom upwardly vertically oriented, (see beam (R1)) then enter said third element (TE) and essentially totally internally reflect from one of said first and second sides thereof, then proceed along an essentially horizontal locus (see beam (R2)), and essentially totally internally reflect from the other of said first (OS1) and second (OS2) sides and proceed along an essentially downward vertically oriented locus, (see beam (R3)), then reflect from the other of said first (OS1) and second (OS2) adjustable mirrored elements and proceed along an essentially horizontally oriented (LB') propagation direction locus which is essentially undeviated and undisplaced from the essentially horizontally oriented locus of said input beam of electromagnetic radiation even when said compensator is caused to rotate about the locus of the beam of electromagnetic radiation, with the result being that retardation is entered between orthogonal components of said input electromagnetic beam of radiation. Also shown are third element lower side (IS3), with indication that it can be shaped as shown by (IS3'), and retain functionality.

Figure 5A:
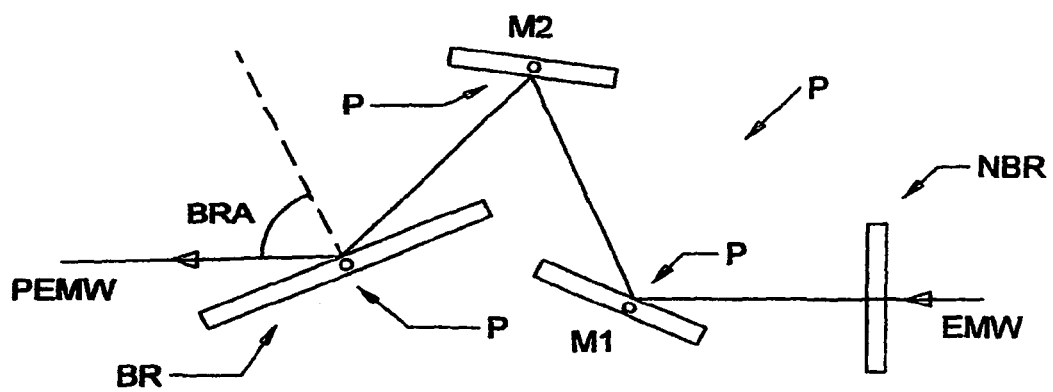
FIG. 5a demonstrates a combined Non-Brewster Angle and Brewster Angle Polarizer system.
Figure 5B:
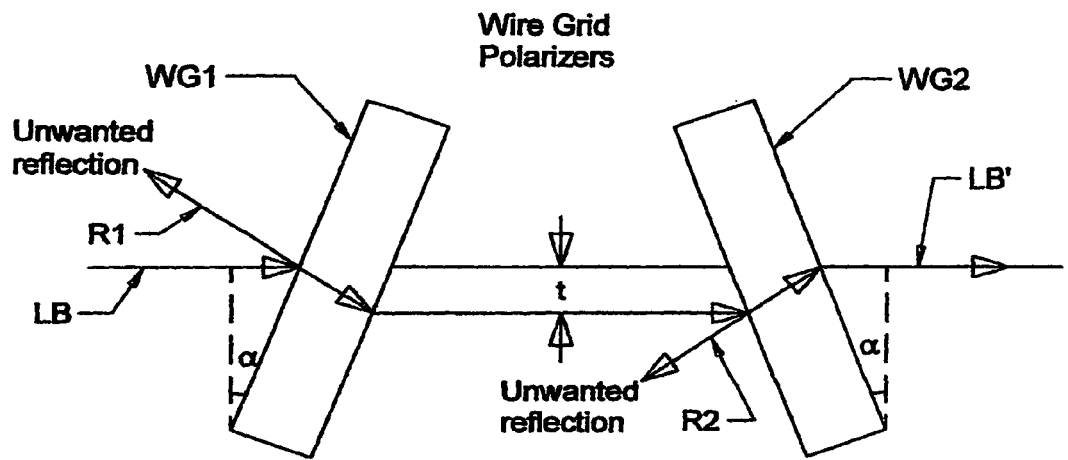
FIG. 5b demonstrates a dual tipped wire grid polarizer system.

FIGS. 5a and 5b demonstrate systems which can be used as Polarizer (P) and Analyzer (A) in FIGS. 1a-1c. FIG. 5a demonstrates a Polarizer (P) comprised of Non-Brewster Angle (NBR) and Non-Brewster (BR) Angle components. Shown is a beam of electromagnetic radiation (EMW) passing demonstrates a compensator design for optional compensators (C) (C') will be present and caused to rotate during data acquisition and the odd bounce image rotating system (OBIRS) will be stepped to various azimuthal angle positions and set motionless during data acquisition, which the fixed linear polarizer (FP) and analyzer (A) (A') are held stationary. That is, the preferred present invention application is in a rotating compensator ellipsometer system, wherein the combination of the fixed polarizer and the odd bounce image rotating system (OBIRS) provide an effective rotatable polarizer. This is useful where a polarizer, (such as tipped wire grid plate polarizers used in the IR wavelength range), is difficult to rotate while maintaining alignment of the components therein and while avoiding deviation and displacement affects between input (EMI) and output (EMO) electromagnetic beams.

FIG. 5b demonstrates an alternative possible polarizer, comprising a dual tipped wire grid polarizer system comprising first (WG1) and second (WG2) wire grid polarizers which have fast axes of polarization oriented with their fast axes parallel to one another, each thereof having first and second essentially parallel surfaces. Note however, that the essentially parallel sides of (WG1) are tipped with respect to the essentially parallel sides of (WG2), as characterized by the angle ($\alpha$). The purpose of angle ($\alpha$) is to divert unwanted reflections (R1) and (R2).

Note that both Polarizers in FIGS. 5a and 5b provide substantially undeviated and undisplaced output beams therefrom, with respect to beams input thereto, even when the polarizer is rotated about the locus of a beam of electromagnetic radiation.

It is to be understood that while preferred embodiments of Polarizers provide a linear polarization as output, the present invention can be used with a substantially linearly polarizing polarizer, or a polarizer which provides partially linearly polarization. In the Claims the term "polarizer" should then be interpreted broadly to mean preferably a linear polarizer, but including polarizers which provide partially linearly polarization. Further, in combination with a Compensator, other polarization states can be achieved.

Figure 6:
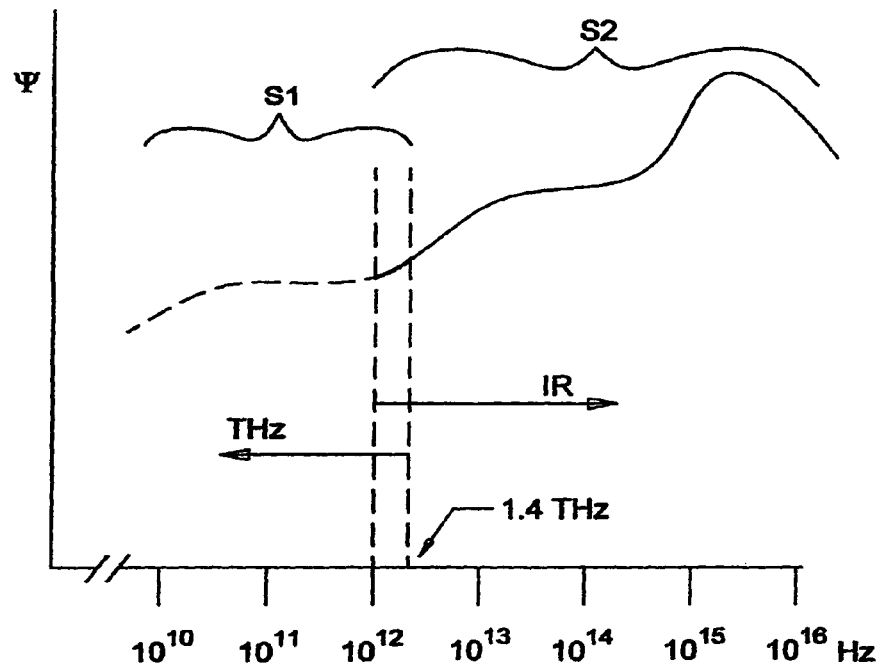
FIG. 6 demonstrates data which can be achieved by application of the Present Invention, including in an overlap frequency range between about 1.0 and 1.4 THz.

FIG. 6 shows that a preferred embodiment of the present invention allows sample investigation in both the THz and IR ranges, (eg. from 300 GHz to abut 1.4 THz, and from about 1.0 THz and higher frequency). Further, it is indicated that below about 1.4 THz a first (S1) is used to provide the electromagnetic radiation, and above about 1.0 THz a second (S2) Source is used to provide the electromagnetic radiation. FIG. 6 shows an overlap in the range of about 1.0 to about 1.4 THZ, and that a present invention system preferably provides the same results, (eg. ellipsometic PSI and/or DELKTA), when Detector output is analyzed to provide, for instance, a Sample characterizing PSI ($\psi$), (or DELTA ($\Delta$)). FIG. 6 should be viewed as demonstrating a concrete and tangible presentation of results which can be achieved by application of the Present Invention.

Figure 7:
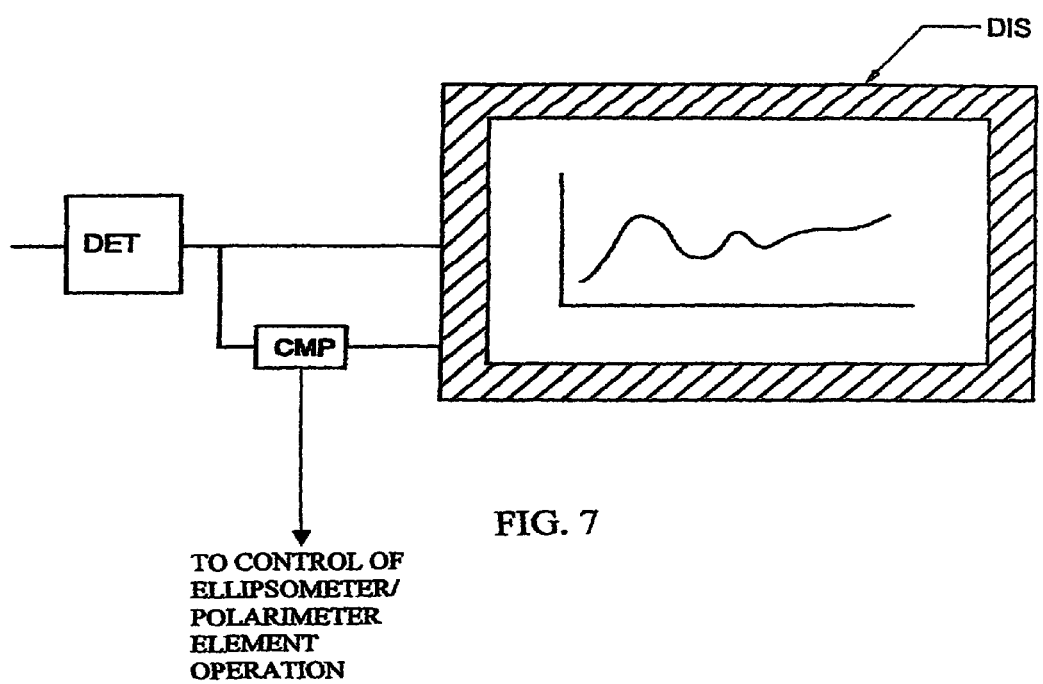
FIG. 7 demonstrates displaying data obtained by practice of the present invention using a computer.

FIG. 7 demonstrates displaying data (DIS) provided by a Detector (DET), (eg. D1, D2 D3 in FIGS. 1a-1d), obtained by practice of the present invention using machine readable media of a computer (CMP), as well as indicates the Computer (CMP) can control Ellipsometer/Polarimeter elements operation.

Finally, in view of recent case law, it is specifically disclosed that a present invention system preferably comprises a Computer System which controls element motion, (eg. stepwise or continuous rotation of a Polarizer (P) and/or Compensator (C, C') and/or Analyzer (A) and/or Odd Bounce Image Rotating System (OB); operation of a Chopper (CH); positioning of a Sample (S); selection of a Source (S1, S2); selection of a Detector (D1, D2, D3); and operation of a Source (S1, S2, S3) and/or Detector (D1, D2, D3). Further, a present invention system comprises a Computer System (CMP) which serves to analyze data provided by a Detector (D1, D2, D3) and Display said data or results of analysis thereof. That is, the present invention can be considered to be a Computer System (CMP) which comprises an Ellipsometer or Polarimeter, which Computer System (CMP) controls operation of elements of said Ellipsometer or Polarimeter to the end that Sample characterizing Data is developed, as well as analysis of said data performed and presentation of said data, or results of analysis thereof.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer or polarimeter system sequentially comprising:
   a backward wave oscillator (BWO);
   optionally a focusing lens;
   a rotatable image rotation system;

a rotatable wire grid polarizer;
a sample supporting stage;
a rotating analyzer;
a Golay cell;
said ellipsometer or polarimeter system further comprising:
an optical chopper;
between said backward wave oscillator and said Golay cell;
such that in use a polarized beam of Terahertz spectral range electromagnetic radiation is provided by said backward wave oscillator, is optionally focused by the focusing lens, has its polarization state rotated by said rotatable image rotation system and passes through said rotatable wire grid polarizer, then impinges on a sample placed on said sample supporting stage, reflects therefrom and passes through said rotating analyzer and enters said Golay cell;
said ellipsometer or polarimeter system being distinguished in that, during data acquisition, the rotatable image rotation system and rotatable wire grid polarizer are functionally stepwise rotated in tandem, wherein said rotatable wire grid polarizer is stepwise rotated through a sequence of angles twice that of the rotatable image rotation system, such that the polarization state of the beam provided to the wire grid polarizer by the rotatable image rotation system, is passed by said rotatable wire grid polarizer even where the polarization state of the polarized beam of Terahertz spectral range electromagnetic radiation from the backward wave oscillator is rotated by 90 degrees.

2. An ellipsometer or polarimeter system as in claim 1 wherein said rotatable image rotation system is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

3. An ellipsometer or polarimeter system as in claim 2, in which the at least one odd bounce (OB) (OB') optical image rotating system consists of a selection from the group consisting of:
three; and
five;
reflective elements.

4. An ellipsometer or polarimeter system as in claim 1, which further comprises at least one beam directing reflecting means.

5. An ellipsometer or polarimeter system as in claim 1, in which sample supporting stage is part of a system for controlling the angle of incidence at which a beam of electromagnetic radiation is caused to approach said sample.

6. An ellipsometer or polarimeter system sequentially comprising:
a backward wave oscillator (BWO);
optionally a focusing lens;
a rotatable or rotating polarizer;
a sample supporting stage;
a rotatable image rotation system;
a rotatable wire grid analyzer;
a Golay cell;
said ellipsometer or polarimeter system further comprising:
an optical chopper;
between said backward wave oscillator and said Golay cell;
such that in use a polarized beam of Terahertz spectral range electromagnetic radiation is provided by said backward wave oscillator, is optionally focused by the focusing lens, has its polarization state rotated by said rotatable or rotating polarizer, then impinges on a sample placed on said sample supporting stage, reflects therefrom and passes through said rotatable image rotation system and rotatable wire grid analyzer and enters said Golay cell;
said ellipsometer or polarimeter system being distinguished in that, during data acquisition, the rotatable image rotation system and rotatable wire grid analyzer are functionally stepwise rotated in tandem, wherein said rotatable wire grid analyzer is stepwise rotated through a sequence of angles twice that of the rotatable image rotation system, such that the polarization state of the beam provided to the rotatable wire grid analyzer by the rotatable image rotation system.

7. An ellipsometer or polarimeter system as in claim 6 wherein said rotatable image rotation system is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

8. An ellipsometer or polarimeter system as in claim 7, in which the at least one odd bounce (OB) (OB') optical image rotating system consists of a selection from the group consisting of:
three; and
five;
reflective elements.

9. An ellipsometer or polarimeter system as in claim 6, which further comprises at least one beam directing reflecting means.

10. An ellipsometer or polarimeter system as in claim 6, in which sample supporting stage is part of a system for controlling the angle of incidence at which a beam of electromagnetic radiation is caused to approach said sample.

11. An ellipsometer or polarimeter system sequentially comprising:
a backward wave oscillator (BWO);
optionally a focusing lens;
a rotatable first wire grid polarizer;
a rotatable second wire grid polarizer;
a sample supporting stage;
a rotating analyzer;
a Golay cell;
said ellipsometer or polarimeter system further comprising:
an optical chopper;
between said backward wave oscillator and said Golay cell;
such that in use a polarized beam of Terahertz spectral range electromagnetic radiation is provided by said backward wave oscillator, is optionally focused by the focusing lens, has its polarization state altered by said first rotatable wire grid polarizer and then by said second rotatable wire grid polarizer, then impinges on a sample placed on said sample supporting stage, reflects therefrom and passes through said rotating analyzer and enters said Golay cell;
said ellipsometer or polarimeter system being distinguished in that said two rotatable wire grid polarizers are functionally operated in tandem such that the polarization state of the beam provided to the second rotatable wire grid polarizer by the first rotatable wire grid polarizer, is passed by said second rotatable wire grid polarizer, where it not be passed were the first rotatable wire grid polarizer not present and the polarization state of the polarized beam of Terahertz spectral range electromagnetic radiation from the backward wave oscillator is rotated by 90 degrees at the location of said sample.

12. An ellipsometer or polarimeter system as in claim 11, which further comprises at least one beam directing reflecting means.

13. An ellipsometer or polarimeter system as in claim 11, in which sample supporting stage is part of a system for controlling the angle of incidence at which a beam of electromagnetic radiation is caused to approach said sample.

14. An ellipsometer or polarimeter system sequentially comprising:
   a backward wave oscillator (BWO);
   optionally a focusing lens;
   a rotatable image rotation system;
   a rotatable wire grid polarizer;
   a sample supporting stage;
   a rotatable analyzer;
   a Golay cell;
said ellipsometer or polarimeter system further comprising:
   an optical chopper; and
   a rotating compensator;
between said backward wave oscillator and said Golay cell; such that in use a polarized beam of Terahertz spectral range electromagnetic radiation is provided by said backward wave oscillator, is optionally focused by the focusing lens, has its polarization state rotated by said rotatable image rotation system and passes through said rotatable wire grid polarizer, then impinges on a sample placed on said sample supporting stage, reflects therefrom and passes through said rotatable analyzer; said Terahertz spectral range electromagnetic radiation also passing through said optical chopper and rotating compensator; and enters said Golay cell;
said ellipsometer or polarimeter system being distinguished in that, during data acquisition while said rotating compensator is caused to continuously rotate, the rotatable image rotation system and rotatable wire grid polarizer are functionally stepwise rotated in tandem, wherein said rotatable wire grid polarizer is stepwise rotated through a sequence of angles twice that of the rotatable image rotation system, such that the polarization state of the beam provided to the wire grid polarizer by the rotatable image rotation system, is passed by said rotatable wire grid polarizer even where the polarization state of the polarized beam of Terahertz spectral range electromagnetic radiation from the backward wave oscillator is rotated by 90 degrees.

15. An ellipsometer or polarimeter system as in claim 14, wherein rotatable analyzer is optionally also stepwise rotated during data acquisition.

16. An ellipsometer or polarimeter system as in claim 14 wherein said rotatable image rotation system is an odd bounce (OB) (OB') optical image rotating system comprising an odd number of at least three reflective elements oriented such that a beam of electromagnetic radiation provided by said source of electromagnetic radiation interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

17. An ellipsometer or polarimeter system as in claim 16, in which the at least one odd bounce (OB) (OB') optical image rotating system consists of a selection from the group consisting of:
   three; and
   five;
reflective elements.

18. An ellipsometer or polarimeter system as in claim 14, which further comprises at least one beam directing reflecting means.

19. An ellipsometer or polarimeter system as in claim 14, in which sample supporting stage is part of a system for controlling the angle of incidence at which a beam of electromagnetic radiation is caused to approach said sample.

20. An ellipsometer or polarimeter system as in claim 14, in which the rotating compensator is present at a selection from the group consisting of:
   between the backward wave oscillator and said sample supporting stage; and
   said sample supporting stage and said Golay Cell;
and which further comprises a linear polarizer on the same side of the sample stage as is the rotating compensator.

21. An ellipsometer or polarimeter system sequentially comprising:
   a backward wave oscillator (BWO);
   optionally a focusing lens;
   optionally a rotatable or rotating polarizer;
   a sample supporting stage;
   a rotatable image rotation system;
   a fixed position analyzer;
   a Golay cell;
said ellipsometer or polarimeter system further comprising:
   an optical chopper;
between said backward wave oscillator and said Golay cell; such that in use a polarized beam of Terahertz spectral range electromagnetic radiation is provided by said backward wave oscillator, is optionally focused by the focusing lens, optionally has its polarization state rotated by said rotatable or rotating polarizer, then impinges on a sample placed on said sample supporting stage, reflects therefrom and passes through said rotatable image rotation system and fixed position analyzer and enters said Golay cell;
said ellipsometer or polarimeter system being distinguished in that, during data acquisition, the rotatable image rotation system is stepwise rotated while the analyzer remains fixed in position.

* * * * *

UNITED STATES PATENT AND TRADEMARK OFFICE
CERTIFICATE OF CORRECTION

PATENT NO. : 8,705,032 B2
APPLICATION NO. : 13/815487
DATED : April 22, 2014
INVENTOR(S) : Herzinger et al.

Page 1 of 1

It is certified that error appears in the above-identified patent and that said Letters Patent is hereby corrected as shown below:

Title page

Item 73 – Assignee

"J.A. Woollam Co., Inc. - should read **"J. A. Woollam Co., Inc., Lincoln, NE;
Board of Regents, University of Nebraska, Lincoln, NE"**

Signed and Sealed this
Fourteenth Day of April, 2015

Michelle K. Lee
*Director of the United States Patent and Trademark Office*